(12) United States Patent
Wang et al.

(10) Patent No.: US 8,213,007 B2
(45) Date of Patent: *Jul. 3, 2012

(54) SPECTRALLY SENSING CHEMICAL AND BIOLOGICAL SUBSTANCES

(75) Inventors: Hong Wang, Cupertino, CA (US); Xun Guo, Sacramento, CA (US); Chunwei Liu, Beijing (CN)

(73) Assignee: Optotrace Technologies, Inc., Mountain View, CA (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/625,970

(22) Filed: Nov. 25, 2009

(65) Prior Publication Data

US 2010/0070197 A1 Mar. 18, 2010

Related U.S. Application Data

(63) Continuation-in-part of application No. 12/403,522, filed on Mar. 13, 2009, now Pat. No. 8,102,525, and a continuation-in-part of application No. 12/246,616, filed on Oct. 7, 2008, now Pat. No. 7,956,997, and a continuation-in-part of application No. 12/176,383, filed on Jul. 20, 2008, now Pat. No. 8,031,335, which is a continuation-in-part of application No. 11/681,157, filed on Mar. 1, 2007, now Pat. No. 7,428,046, which is a continuation of application No. 10/987,842, filed on Nov. 12, 2004, now Pat. No. 7,242,469, which is a continuation-in-part of application No. 10/852,787, filed on May 24, 2004, now Pat. No. 7,384,792.

(60) Provisional application No. 60/473,283, filed on May 27, 2003, provisional application No. 60/473,287, filed on May 27, 2003, provisional application No. 60/520,222, filed on Nov. 17, 2003.

(51) Int. Cl.
*G01J 3/28* (2006.01)
(52) U.S. Cl. ........................................ 356/326; 356/301
(58) Field of Classification Search ............ 356/301.326
See application file for complete search history.

(56) References Cited

U.S. PATENT DOCUMENTS

| | | | |
|---|---|---|---|
| 4,933,274 A | 6/1990 | Sanford | |
| 5,017,007 A | 5/1991 | Milne | |
| 5,210,590 A * | 5/1993 | Landa et al. | 356/319 |
| 5,244,788 A | 9/1993 | Hubscher | |
| 5,455,673 A * | 10/1995 | Alsmeyer et al. | 356/301 |
| 5,527,712 A | 6/1996 | Sheehy | |
| 5,814,516 A * | 9/1998 | Vo-Dinh | 356/301 |
| 5,864,397 A | 1/1999 | Vo-Dinh | |
| 6,361,861 B2 | 3/2002 | Gao | |

(Continued)

*Primary Examiner* — Kara E Geisel
(74) *Attorney, Agent, or Firm* — SV Patent Service

(57) ABSTRACT

A sensor-network system for spectrally sensing a chemical or biological substance includes a plurality of probe assemblies that each includes a sensor comprising a nano structured surface, wherein the nano structured surface can adsorb molecules of a sample material captured adjacent to the sensor; a laser configured to emit a laser beam to illuminate the molecules adsorbed to the nano structured surface, and a spectrometer that can obtain spectral data from light scattered by the molecules adsorbed to the nano structured surface. A control center includes a computer storage configured to store spectral signatures each associated with a chemical or biological substance and a spectral analyzer that can determine a spectral signature matching at least one of the spectral signatures stored in the computer storage thereby to identify, in the sample material, the chemical or biological substance associated with the one of the spectral signatures.

35 Claims, 34 Drawing Sheets

U.S. PATENT DOCUMENTS

| | | |
|---|---|---|
| 6,406,777 B1 | 6/2002 | Boss |
| 6,614,523 B1 | 9/2003 | Boss |
| 2002/0123050 A1 | 9/2002 | Poponin |
| 2003/0059820 A1 | 3/2003 | Vo-Dinh |
| 2003/0142309 A1* | 7/2003 | Kuebler et al. ............... 356/338 |
| 2003/0175472 A1 | 9/2003 | Den |
| 2004/0106203 A1 | 6/2004 | Stasiak |
| 2005/0136552 A1 | 6/2005 | Buechler |
| 2005/0162646 A1* | 7/2005 | Tedesco et al. ............... 356/301 |
| 2007/0048746 A1* | 3/2007 | Su et al. ............................ 435/6 |
| 2007/0056388 A1* | 3/2007 | Henry et al. ............... 73/863.12 |
| 2011/0212512 A1* | 9/2011 | Wang et al. ................... 356/301 |

* cited by examiner

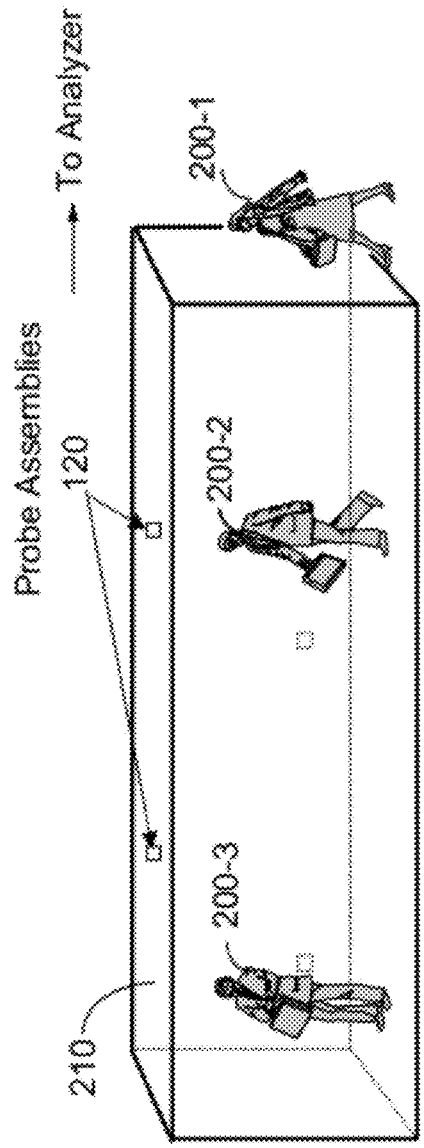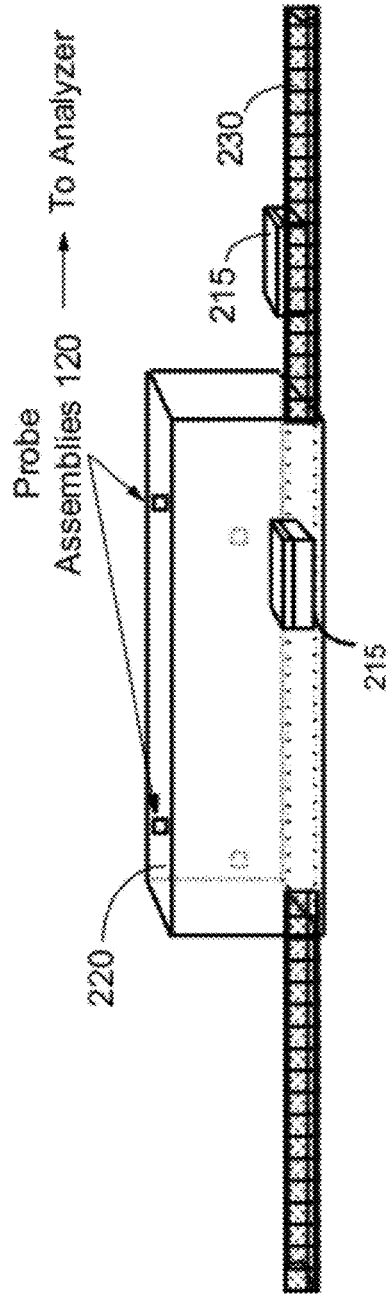

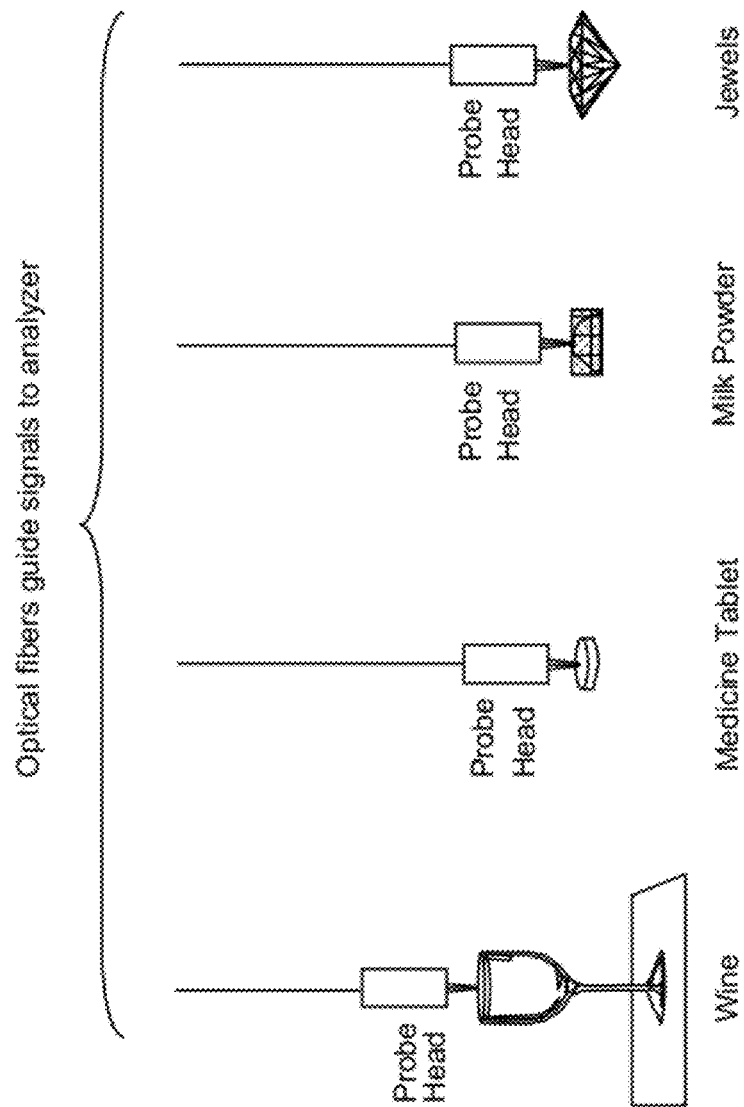

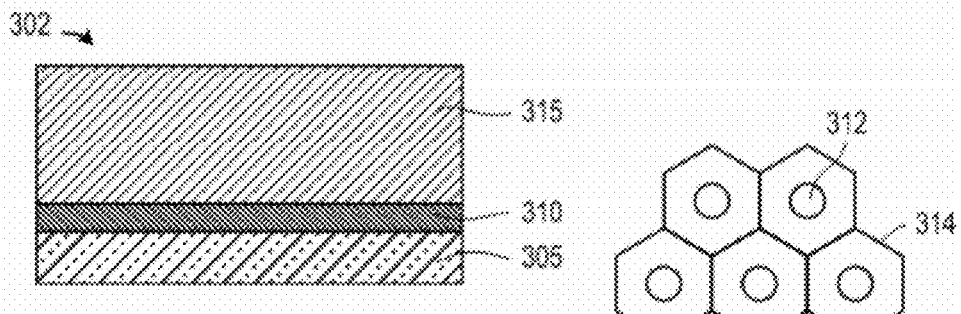
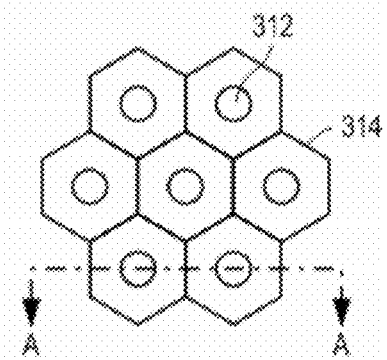
FIG. 10
FIG. 11B
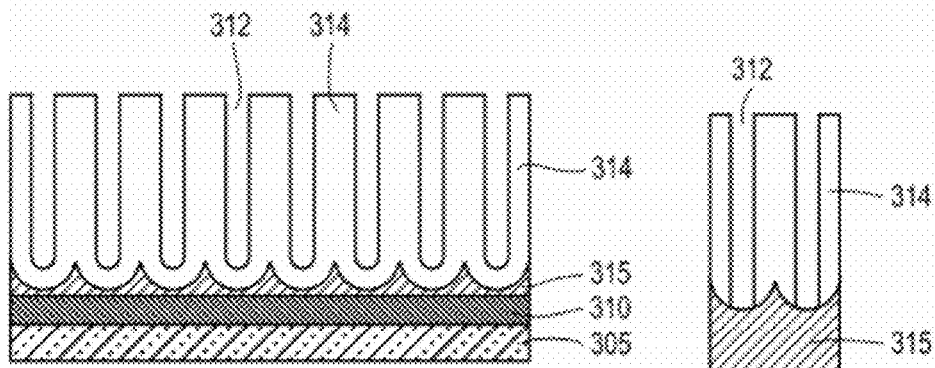
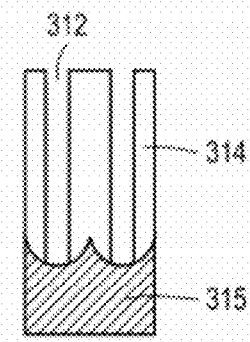
FIG. 11A
SECTION A-A
FIG. 11C
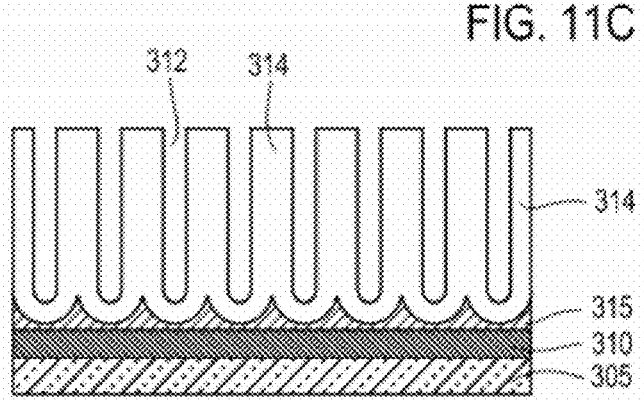
FIG. 12

SPECTRALLY SENSING CHEMICAL AND BIOLOGICAL SUBSTANCES

The present application is a Continuation-in-Part (CIP) patent application of and claims priority to commonly assigned U.S. patent application Ser. No. 12/403,522, entitled "Improved systems and methods for detecting chemicals and biological substances", filed Mar. 13, 2009, now U.S. Pat. No. 8,102,525 U.S. patent application Ser. No. 12/246,616, entitled "System and methods for food safety detection", filed on Oct. 7, 2008 now U.S. Pat. No. 7,956,997, and U.S. patent application Ser. No. 12/176,383, entitled "Non-invasive disease diagnosis using light scattering probe", filed on Jul. 20, 2008 now U.S. Pat. No. 8,031,335. U.S. patent application Ser. No. 12/176,383 is a CIP of commonly assigned U.S. patent application Ser. No. 11/681,157 (now issued as U.S. Pat. No. 7,428,046), entitled "Trace chemical optical probe", filed on Mar. 1, 2007. U.S. patent application Ser. No. 11/681,157 is a continuation application of commonly assigned U.S. patent application Ser. No. 10/987,842, filed on Nov. 12, 2004 (now issued as U.S. Pat. No. 7,242,469). U.S. patent application Ser. No. 10/987,842 is a CIP patent application of U.S. patent application Ser. No. 10/852,787 (now issued as U.S. Pat. No. 7,384,792) filed on May 24, 2004. U.S. patent application Ser. No. 10/852,787 claims priority to Provisional Patent Applications 60/473,283 and 60/473,287 filed on May 27, 2003, and Provisional Patent Application 60/520,222 filed on Nov. 17, 2003. The disclosures of these related patent applications are incorporated herein by reference.

BACKGROUND

This invention generally relates to detection of chemical and biological substances by a light scattering probe and a chemical sensor.

Light scattering methods such as Raman spectroscopy are known to be capable of identifying chemicals and biological agents. A major limitation associated with Raman spectroscopy is that the Raman scattering signals from chemicals and biological agents tend to be very weak. Although many attempts have been made to increase Raman scattering intensity, such efforts have not yielded practical and economical detectors based on Raman spectroscopy. As a result, Raman scattering so far only has very limited applications in sensing chemicals and biological agents.

A need therefore continues to exist for effective and practical spectroscopy-based detectors for trace amount of chemical or biological substances.

SUMMARY

In one aspect, the present invention relates to a sensor-network system for spectrally sensing a chemical or biological substance. The system includes a plurality of probe assemblies each comprising a sensor comprising a nano structured surface that can adsorb molecules of a sample material captured adjacent to the sensor; a laser that can emit a laser beam to illuminate the molecules adsorbed to the nano structured surface; and a spectrometer that can obtain spectral data from light scattered by the molecules adsorbed to the nano structured surface. The system also includes a control center comprising: a computer storage that can store one or more spectral signatures each associated with a chemical or biological substance; and a spectral analyzer in communication with the computer storage, wherein the spectral analyzer can determine, in the spectral data, a spectral signature matching at least one of the spectral signatures stored in the computer storage thereby to identify, in the sample material, the chemical or biological substance associated with the one of the spectral signatures.

In another general aspect, the present invention relates to a sensor-network system for spectrally sensing a chemical or biological substance. The system includes a plurality of probe assemblies at a plurality of locations, each probe assembly comprising: a sensor that can receive molecules of a sample material captured adjacent to the sensor; a laser that can emit a laser beam to illuminate the molecules; and a spectrometer that can obtain spectral data from light scattered by the molecules in the sensor. The system also includes a control center comprising: a computer storage that can store one or more spectral signatures each associated with a chemical or biological substance; a spectral analyzer in communication with the computer storage, wherein the spectral analyzer can determine, in the spectral data, a spectral signature matching at least one of the spectral signatures stored in the computer storage thereby to identify, in the sample material, the chemical or biological substance associated with the one of the spectral signatures; and a processor that can correlate a location the sample material at a specific a time using the spectral data obtained from two or more of the plurality of probe assemblies and using the locations of the two or more of the plurality of probe assemblies. A processor in a control center can then take action to generate a response to the location of the detected chemical or biological agent.

In another general aspect, the present invention relates to a sensor-network system for spectrally sensing a chemical or biological substance. The system includes a plurality of probe assemblies each comprising: a sensor comprising a nano structured surface that can adsorb molecules of a sample material captured adjacent to the sensor; and a laser that can emit a laser beam to illuminate the molecules adsorbed to the nano structured surface, wherein the probe assembly is configured to transmit the light scattered by the molecules adsorbed to the nano structured surface to a control center in an optical fiber. The system also includes a control center comprising: an optical multiplexer configured to receive the light scattered by the molecules adsorbed to the nano structured surface from the plurality of probe assemblies in a plurality of channels and output scattered light in one of the plurality of channels; a spectrometer that can obtain spectral data from the scattered light in one of the plurality of channels output by the optical multiplexer; a computer storage that can store one or more spectral signatures each associated with a chemical or biological substance; and a spectral analyzer in communication with the computer storage, wherein the spectral analyzer can determine, in the spectral data, a spectral signature matching at least one of the spectral signatures stored in the computer storage thereby to identify, in the sample material, the chemical or biological substance associated with the one of the spectral signatures.

In another general aspect, the present invention relates to a method for spectrally sensing a chemical or biological substance. The method includes illuminating the molecules of a sample material by a laser beam emitted by a laser device at a first site; obtaining spectral data from the light scattered by the molecules by a spectrometer at the first site; transmitting a wireless signal comprising the spectral data from the first site to a second site; receiving and extracting the spectral data from the wireless signal by a wireless server at a second site; determining, by a spectral analyzer in the spectral data, the existence of a spectral signature associated with a chemical or biological substance around a predetermined wavelength;

and identifying, by a computer processor, the chemical or biological substance in the sample material based on the spectral signature.

In another general aspect, the present invention relates to a method for detecting a chemical or biological substance. The method includes introducing a sample material into a sample solution containing nano particles; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another general aspect, the present invention relates to a method for detecting a chemical or biological substance. The method includes introducing a sample material into a sample solution containing nano particles having an average dimension in a range from about 5 nm to about 500 nm, wherein the nano particles have a size distribution characterized by an average dimension and a width, wherein the ratio of the width to the average dimension is in a range from about 0.01 to about 3, wherein the nano particles comprise a magnetic or ferromagnetic material; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another general aspect, the present invention relates to a method for detecting a chemical or biological substance. The method includes introducing a sample material into a sample solution, wherein the sample solution comprises nano particles having an average dimension in a range from about 5 nm to about 500 nm, wherein the nano particles have a size distribution characterized by an average particle dimension and a particle-dimension distribution width, wherein the ratio of the particle-dimension distribution width to the average particle dimension is in a range from about 0.01 to about 3; introducing an ionic material comprising multi-valence ions into the sample solution; illuminating the sample solution containing the sample material and the nano particles by a laser beam; collecting light scattered by the sample material and the nano particles in the sample solution; obtaining a Raman spectrum from the light scattered by the sample material and the nano particles in the sample solution; determining the existence of a spectral signature associated with a chemical or biological substance around a predetermined wavelength in the Raman spectrum; and identifying the chemical or biological substance in the sample material based on the spectral signature in the Raman spectrum.

In another general aspect, the present invention relates to a method for detecting an ingredient in a food product. The method includes establishing a spectral signature in a Raman spectrum obtained from a chemical substance; allowing a food sample solution obtained from a food product to come to contact with a first nano-scale surface structure in a first sensor, wherein the first sensor comprises a substrate, wherein the nano-scale surface structure comprises a plurality of columns over the substrate or a plurality of holes in the substrate; illuminating the food sample solution and the first nano-scale surface structure on the first sensor by a laser beam; scattering the laser beam by the food sample solution and the first nano-scale surface structure to produce a scattered light; obtaining a first Raman spectrum from the scattered light using a spectral analyzer; and identifying the spectral signature in the first Raman spectrum to determine the existence of the chemical substance in the food product.

In another general aspect, the present invention relates to a method for detecting an ingredient in a food product. The method includes allowing a reference sample solution containing the chemical substance to come to contact with a first nano-scale surface structure in a first sensor; obtaining a first Raman spectrum from the reference solution and the nano surface to establish a spectral signature in the first Raman spectrum for the chemical substance; allowing a food sample solution obtained from a food product to come to contact with a second nano-scale surface structure in a second sensor; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; and identifying the spectral signature in the second Raman spectrum to determine the existence of the chemical substance in the food product.

In another general aspect, the present invention relates to a method for detecting an ingredient in a food product. The method includes allowing a reference sample solution containing the chemical substance to come to contact with a first nano-scale surface structure in a first sensor, wherein the first nano-scale surface structure includes a plurality of nano particles on a surface of the first sensor, or a plurality of columns or holes having an average neighboring distance in a range from 10 nanometers to 1,000 nanometers; obtaining a first Raman spectrum from the reference solution and the nano surface to establish a spectral signature around a predetermined wavelength in the first Raman spectrum for the chemical substance, wherein the spectral signature includes at least one spectral peak around the predetermined wavelength in the first Raman spectrum; allowing a food sample solution obtained from a food product to come to contact with a second nano-scale surface structure in a second sensor, wherein the first sensor and the second sensor have substantially the same nano surface structures; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; identifying the spectral signature around the predetermined wavelength in the second Raman spectrum to determine the existence of the chemical substance in the food product, wherein the step of identifying comprises determining if the spectral peak in the Raman spectrum or a signal-to-noise ratio for the spectral peak is above a pre-determined threshold value; and positively identifying the chemical substance if the spectral peak or the signal-to-noise ratio is above the pre-determined threshold value.

Implementations of the system may include one or more of the following. At least one of the plurality of probe assemblies can further include collection optics that can collect the light scattered by molecules in the sensor and direct the scattered light to the spectrometer. The spectral data can be transmitted from the probe assemblies to the control center via a wired computer network. The control center can further include an alert and response system in communication with the spectral analyzer, wherein the alert and response system is configured to send out an alert signal when the identified chemical or biological substance is a hazardous material. The system can further include a first antenna in communication with the one of the probe assemblies, wherein the first antenna is configured to transmit a first wireless signal comprising the spectral data, wherein the control center can include a second antenna configured to receive the first wireless signal; and a wireless router in communication with the spectral analyzer, wherein the wireless router can extract the spectral data from the first wireless signal. The control center can further include an alert and response system in communication with the spectral analyzer and the wireless router, wherein the alert and response system can send out an alert signal when the identified chemical or biological substance is a hazardous material, wherein the wireless router can transmit a second wireless signal comprising the alert signal. The nano structured surface on the sensor can include nano particles supplied by a solution. The substrate can include a substantially flat surface on which the nano particles are disposed. The plurality of probe assemblies can be installed in or around a building, an airport, a custom, a conveyance system for cargo or luggage, a doctor's office, a check station on a road, a harbor, in a vehicle, a ship, a submarine, an airplane, a train, a subway, an industrial site, a resort area, a shopping mall, a research Lab, a school, or a water source. The spectral data can include information about a Raman spectrum. The sample material can be extracted from a food product. The sample material can include a body fluid obtained from a person or an animal, the method further comprising: diagnosing a disease in a person or an animal based on the spectral signature determined in the Raman spectrum. The plurality of probe assemblies can be disposed for security monitoring, wherein the sample material to be captured adjacent to the sensor comprises a material for a chemical weapon, an explosive material, a flammable material, a narcotic drugs, or a radioactive material. Embodiments may include one or more of the following advantages.

The disclosed systems and methods provide simple and non-invasive approach to detect a disease in a patient. The disclosed systems are portable and easy to operate, and are thus ideal for being used for early disease prevention, and in-field drug usage screening. The disclosed systems and methods are suitable for early detect and diagnosis. The disclosed systems and methods also have short testing cycle time, and can therefore be very helpful for monitoring progresses in the treatment of diseases and drug use. The disclosed systems and methods can detect a wide range of disease such as cancers including but not limited to oral cancer, breast cancer, lung cancer, stomach cancer, ulcer cancer, ovarian cancer, uterus cancer, cervical cancer, esophageal cancer, thyroid cancer, larynx cancer, leukemia, colon cancer, bladder cancer, prostate cancer, bronchus cancer, pancreas cancer, and liver cirrhosis, a failing kidney, diabetes, HIV, smoking status as well as illicit drug use.

In another aspect, the present application provides convenient and application specific systems and methods for food inspection. Applications can include detection of harmful and un-authorized ingredients in food products (i.e., illegal food additives), and concentration of useful ingredients in food products. The disclosed systems and methods can implemented as portable devices and easy procedures to be used for food inspection in the filed with short test time.

In another general aspect, the disclosed system can detect trace biological or chemical substances using a light scattering probe and a chemical sensor. A solution containing the substance is transferred to the chemical sensor to allow molecules of the substance to be adsorbed on a nano structured surface on the chemical sensor. The substance is determined by illuminating laser light at the nano structured surface on the chemical sensor.

In another general aspect, the disclosed system can detect trace biological or chemical substance using a light scattering probe and a solution containing nano particles. The substance is dissolved in the solution allow molecules of the substance to be adsorbed on to the surfaces of the nano particles. A laser beam illuminates the solution directly. The light scattered by the nano particles is collected by the light scattering probe to determine the trace biological or chemical substances.

In another general aspect, the disclosed network of Raman spectral sensors allows effective sensing of chemical and biological substances in a wide area in the field. The Raman spectral sensing signals from the sensors can be instantaneously communicated to a control center in a wired or wireless network. The control center can include a database storing spectral signatures for a plurality of target chemical and biological substances. The signals can be analyzed by a local or a central system module to identify target chemical or biological substances in real time. The control center can correlate Raman spectral sensing signals from different sensors in the network to determine the position and the occurring time of the source for the detected chemical or biological substance. The control center can include an alert system that can communicate the detection of certain target chemical or biological substances to personnel by wired or wireless system which include but not limited to via emails, instant messaging, automated calls and blogs. The disclosed sensing network is suitable for a wide range of applications such as food safety, forensic/security environmental application including pollution sensing in the air, water, or soul, medical and health care, control and prevention of contagious diseases and epidemics, industrial process monitoring, and product authentication application. The disclosed sensing network can also be used in remote diagnosis of diseases in patients or animals by doctors and other medical specialists.

The disclosed light sensing systems and methods can be used in a wide range of applications. Examples of such applications include detection of explosives and biochemical weapons for homeland security, detection of illegal drugs, food inspection, disease diagnosis, product authentication, environmental monitoring, industrial hygiene, and industrial process monitoring.

BRIEF DESCRIPTION OF THE DRAWINGS

The following drawings, which are incorporated in and from a part of the specification, illustrate embodiments of the present invention and, together with the description, serve to explain the principles of the invention.

FIGS. 3A and 3B are schematic diagrams respectively showing inspections of passengers and luggage using a Raman scattering probe at an airport.

FIG. 6D is a schematic diagram showing detection of counterfeit merchandise, inspection of safety and quality food and beverages, and drug authentication using a multi-channel sensing system.

FIG. 10 is a cross-sectional view of a multi-layer layer structure to be used for fabricating a nano-structure.

FIG. 11A is a cross-sectional view showing the formation of holes by anodization in the multi-layer layer structure of FIG. 10.

FIG. 11B is a top view of the multi-layer layer structure of FIG. 11A.

FIG. 11C is a cross-sectional view of the multi-layer layer structure along the line A-A in FIG. 11B.

FIG. 12 is a cross-sectional view of the nano-structure formed on the multi-layer layer structure after a wet chemical etch or chemical mechanical polishing (CMP).

DETAILED DESCRIPTION

Figure 1:
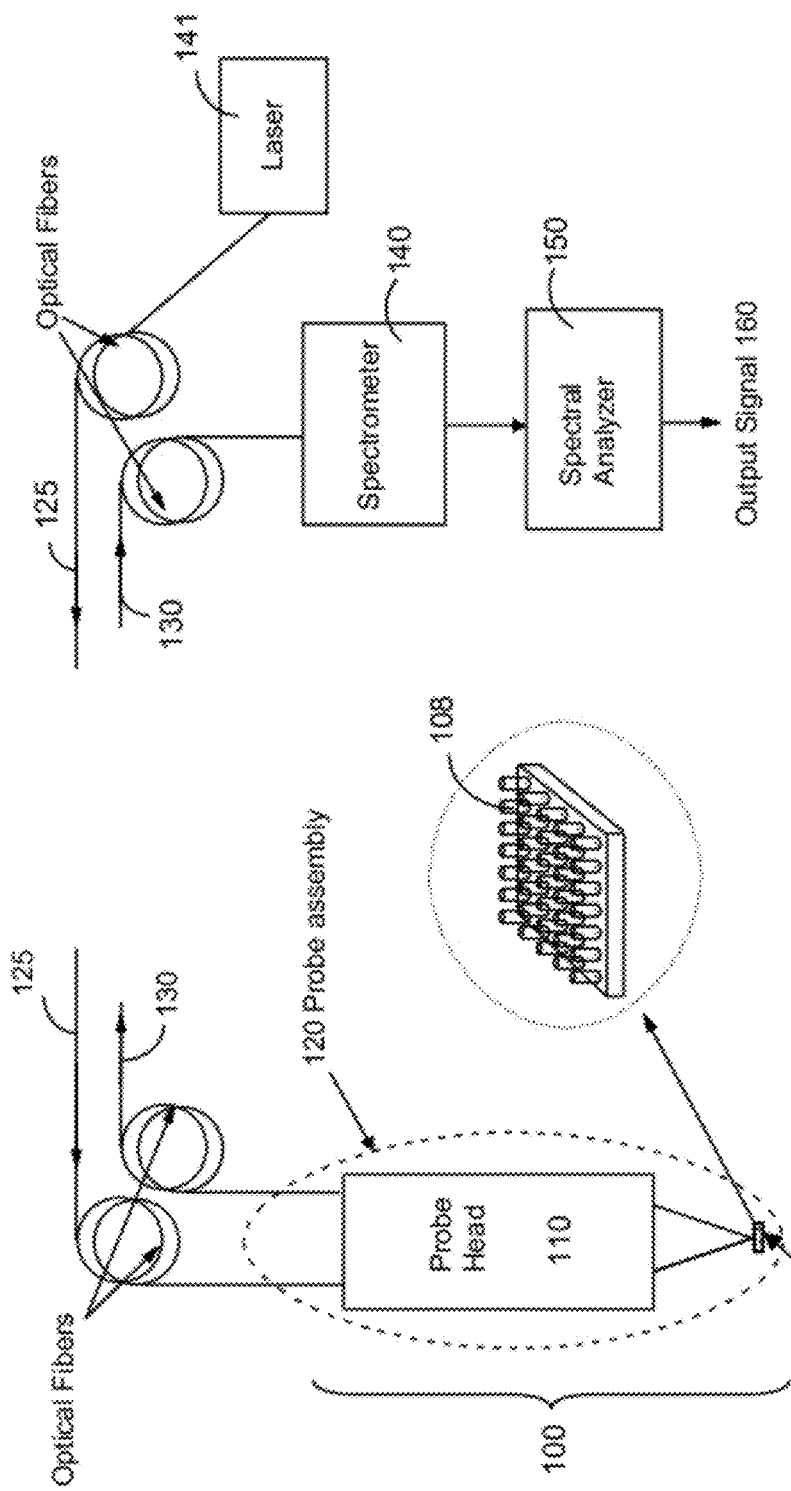
FIGS. 1A-1C illustrate exemplified system for detection of chemical and biological substances using a Raman Scattering probe.

FIGS. 1A-1C respectively illustrate a system for detecting trace chemical or biological substances using Surface-Enhance Raman Scattering. Referring to FIG. 1A, a light scattering probe 100 includes a probe head 110, and a sensor 105 positioned adjacent to the probe head 110. The sensor 105 includes a nano surface structure. For example, the nano surface structure can include a plurality of nano rods 108 (shown FIG. 1B), a plurality of nano holes, or other surface structures having dimensions at nanometer scale. In some embodiments, as described below, a nano structured surface structures can be prepared by coating the surface of the sensor 105 of a solution containing a colloidal suspension of nano particles. The solution can be subsequently evaporated to deposit the nano particles on the surface.

In some embodiments, a sample fluid can be introduced to the nano rods 108 in the sensor 105. The sample fluid can include a body fluid obtained from a patient or an illicit drug user for disease diagnosis and drug use determination. Examples of the body fluid include blood, saliva, urine, serum, tear, sweat, stomach fluid, hydrothorax, ascites, CSF, sperm, and a secrete body fluid. The sample fluid can also comprise a food sample for detecting harmful or illegal additives in a food product to ensure food safety. Examples of good products include dairy products such as milk, milk powder, baby formula, cheese, yogurt, ice cream, milk-containing food products such as milk-containing candies, cake and cookies, and protein-containing food products. The probe head 110 and the sensor 105 can be enclosed in a probe assembly 120. The probe assembly 120 can be depressurized by a vacuum pump to reduce the contamination of the sensing surfaces by foreign substances.

A laser beam emitted by a laser 141 is guided by an optical fiber 125, as shown in FIG. 1C, to the probed head and to illuminate the nano surface structure on the sensor 105 (FIG. 1A). The light scattered by the sample solution on the nano-surface of the sensor 105 is collected by the probe head 110 and guided to a spectrometer 140 by an optical fiber 130. A Raman spectrum of the scattered light is obtained by a spectral analyzer 150 using the output of the spectrometer 140. One or more spectral signatures in the Raman spectrum are identified and compared with predetermined spectral signatures for various molecules. An output signal 160 indicates identification of a disease when a threshold of certain molecules under detection is exceeded. In the present specification, the term "spectral signature" refers to one or more spectral peaks, one or more spectral valleys, and other spectral shapes such as relative peak height, peak line width, peak shape which characterize one or more molecular bonds in a biological, medical, or chemical substance.

Figure 2:
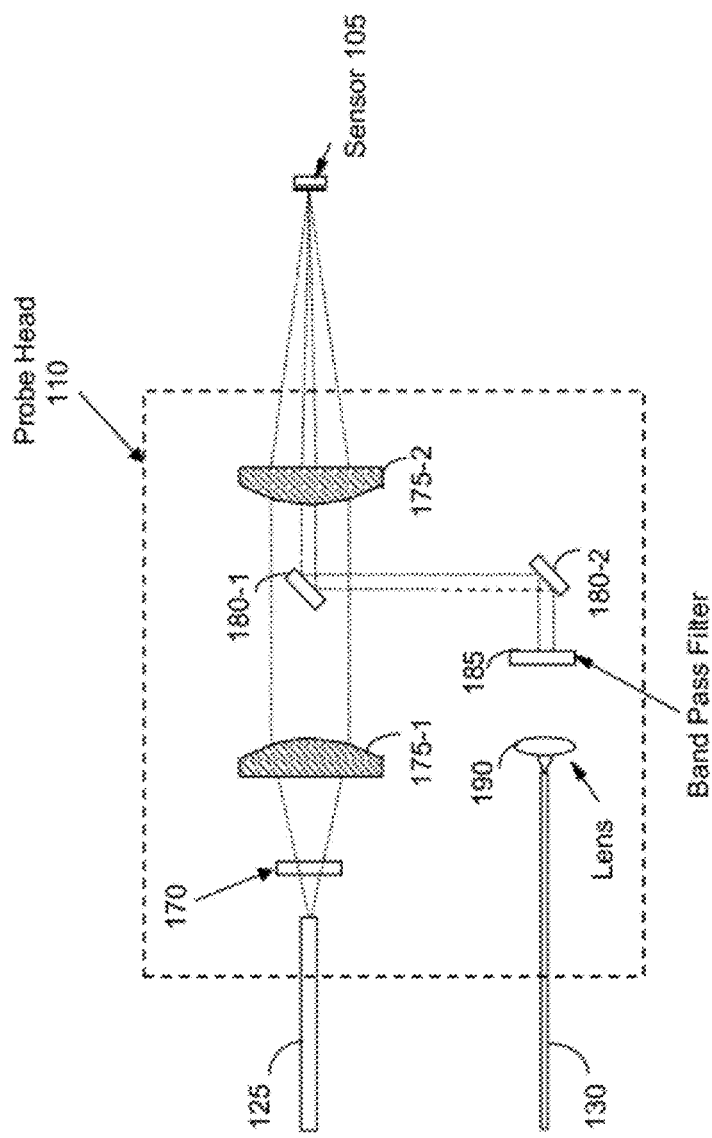
FIG. 2A illustrates an exemplified probe head for Raman scattering probe compatible with FIGS. 1A-1C.

Referring to FIG. 2, the probe head 110 receives a laser beam from an input optical fiber 125. The laser beam passes through a band ejection filter 170 and lenses 175-1 and 175-2 to project onto the sensor 105. A scattering light from the sensor 105 is directed by a group of mirrors 180-1 and 180-2 to pass through another band-pass filter 185 and further collimated by a collimating lens 190 to enter the collection optical fiber 130.

The trace chemicals or biological agents to be detected can be provided in the form of a gas, a liquid, a solid, a sol gel, or an aerosol. The molecules are adsorbed onto the nano surface or nano particles of the sensor 105. Such adsorbed molecules have much larger scattering cross section under laser beam illustration than that they are in free form in a gas, a liquid, a solid, a sol gel, or an aerosol. When a laser beam illuminates the adsorbed molecules, Raman scattering spectrum of the molecules can be obtained. Targeted chemicals or biological agents can be identified using predetermined Raman spectral signatures for the molecules.

FIG. 3A shows an exemplified application of Surface-Enhance Raman Scattering in the area of transportation safety. Passengers 200-1, 200-2, and 200-3 walking through a passageway tunnel 210 are screened. One or more probe assemblies 120 with embedded sensor 105 are placed in the passageway tunnel 210. The probe assemblies 120 can be connected by fibers to a spectral analyzer 150 in a nearby or remote office. In each probe assembly 120, a probe head and a sensor are packaged together. The probe head is aligned to point to the sensing surface of a sensor 105. The passageway tunnel 210 can be forced ventilated and under little negative pressure and/or little higher temperature to increase evaporation of harmful materials. If a passenger (e.g., the passenger 200-2) carries an explosive material, a harmful chemical, a chemical weapon, a bio-chemical weapon, a nuclear weapon or a narcotic drug, a trace amount of such materials will volatilize into air such that molecules of the material can be adsorbed onto the surface of a sensor through a specially designed sample collection system (a detailed example is disclosed in the above referenced and commonly assigned U.S. Pat. No. 7,384,792). The Raman Spectra can be recorded and compared with the spectral signatures of known substances stored at a database at a central office. As soon as the harmful materials are detected, an alarm signal will be triggered. Appropriate security responses will be activated.

Referring to FIG. 3B, cargos 215 for freight transportation are carried by a conveyer 230 to pass through cargo screening channel 220. Probe assemblies 120 each embedded with a sensor 105 are placed around the cargo screen channel 220. The probe assemblies 120 can be connected with fibers to the spectral analyzer 150 in office near or far away from it. The probe head 120 is aligned to the surface of a sensor 105 and they are packaged together to detect any explosives, chemical or biochemical weapon, or harmful chemicals enclosed in the luggage 215. This configuration can be implemented in other applications such as checked-in luggage for passenger air travel, mail stations, railway stations, custom inspection areas, traffic control zones, etc. This configuration can be easily implemented to detect gun powders and other explosives, flammable materials including liquids, or other hazardous materials.

Wired Sensor Network

Figure 4A:
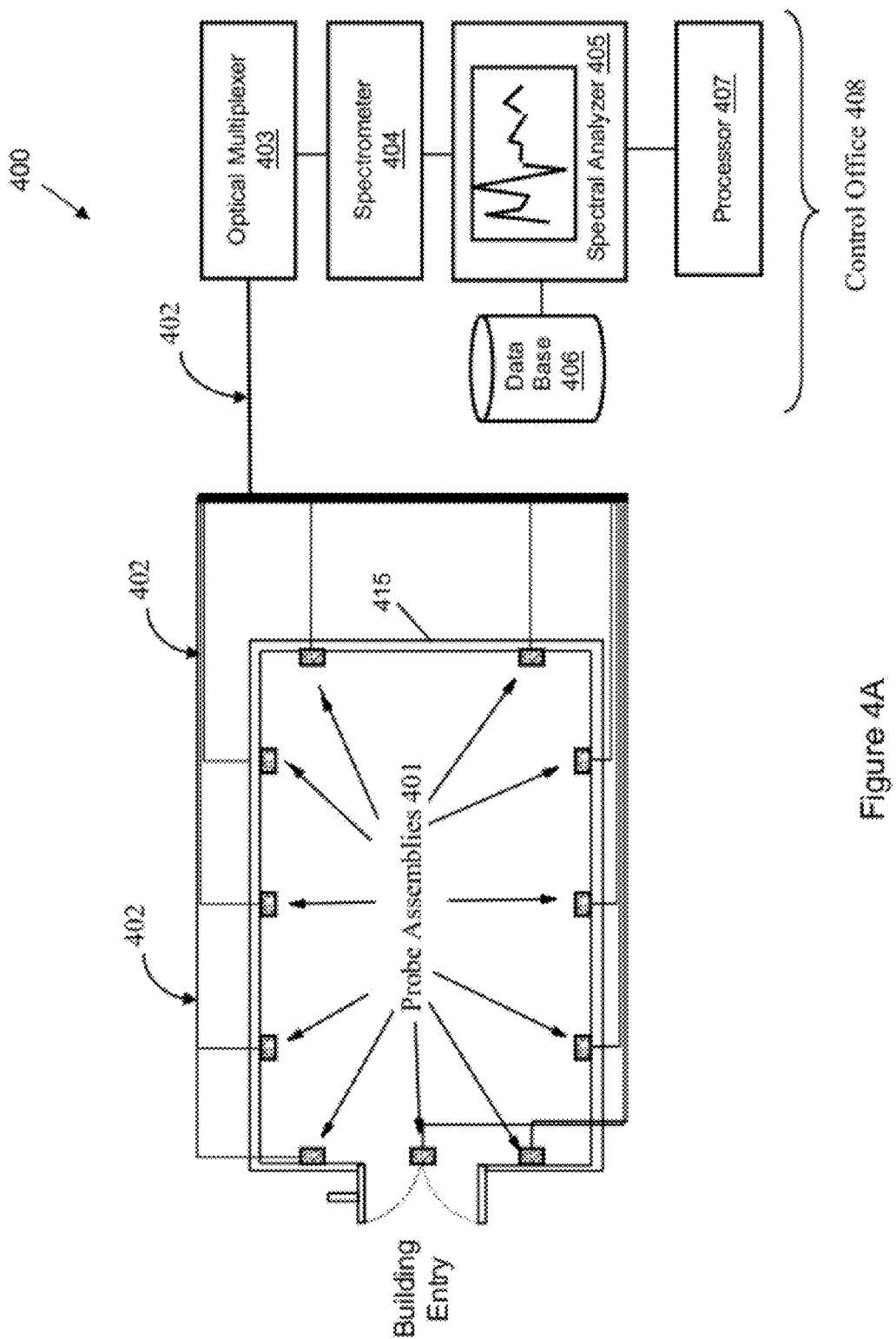
FIG. 4A is a schematic diagram for a network of wired-line connected Raman scattering probes for monitoring the safety of a building.

Referring to FIG. 4A, a sensor-network system 400 is used in safety monitoring of a public building such as airport, railway or bus stations, ballpark buildings, Federal buildings, auditoriums, theaters, courthouses, shopping mall and other public buildings. A plurality of probe assemblies 401 are installed at various locations in a public building 415 or others protected areas. Each probe assembly 401 includes a probe head and a sensor (not separately shown in FIG. 4A). The probe head can be implemented similar to the probe head 110 (FIG. 1A) but can include a laser device. The sensor is compatible with the sensor 105 (FIG. 1B) that includes a nano surface structure on the surface. The sensor can also be a liquid solution that is configured to receive sample material to be detected. The solution can also include nano particles configured to adsorb the molecules of the sample materials. The probe assemblies 401 are applied to monitor many different molecular substances to provide earlier detection of any dangerous or harmful chemicals enter into the monitor areas. The optical signals collected by the probe assemblies 401 can be fed in multiple channels via optical fibers 402 to an optical multiplexer 403 at a control office 408. The optical signals are analyzed by a spectrometer 404 to produce spectral signals, which are analyzed by a spectral analyzer 405. Spectral signatures are identified in the spectral data by the processor 407 using pre-stored spectral signatures in a data based 406. Particular examples of hazardous material monitoring include, but not limited to detection of explosive materials including liquids, chemical or biochemical weapons including anthrax, flammable liquid materials, drugs, and so on.

Wireless Sensor Network

Figure 4B:
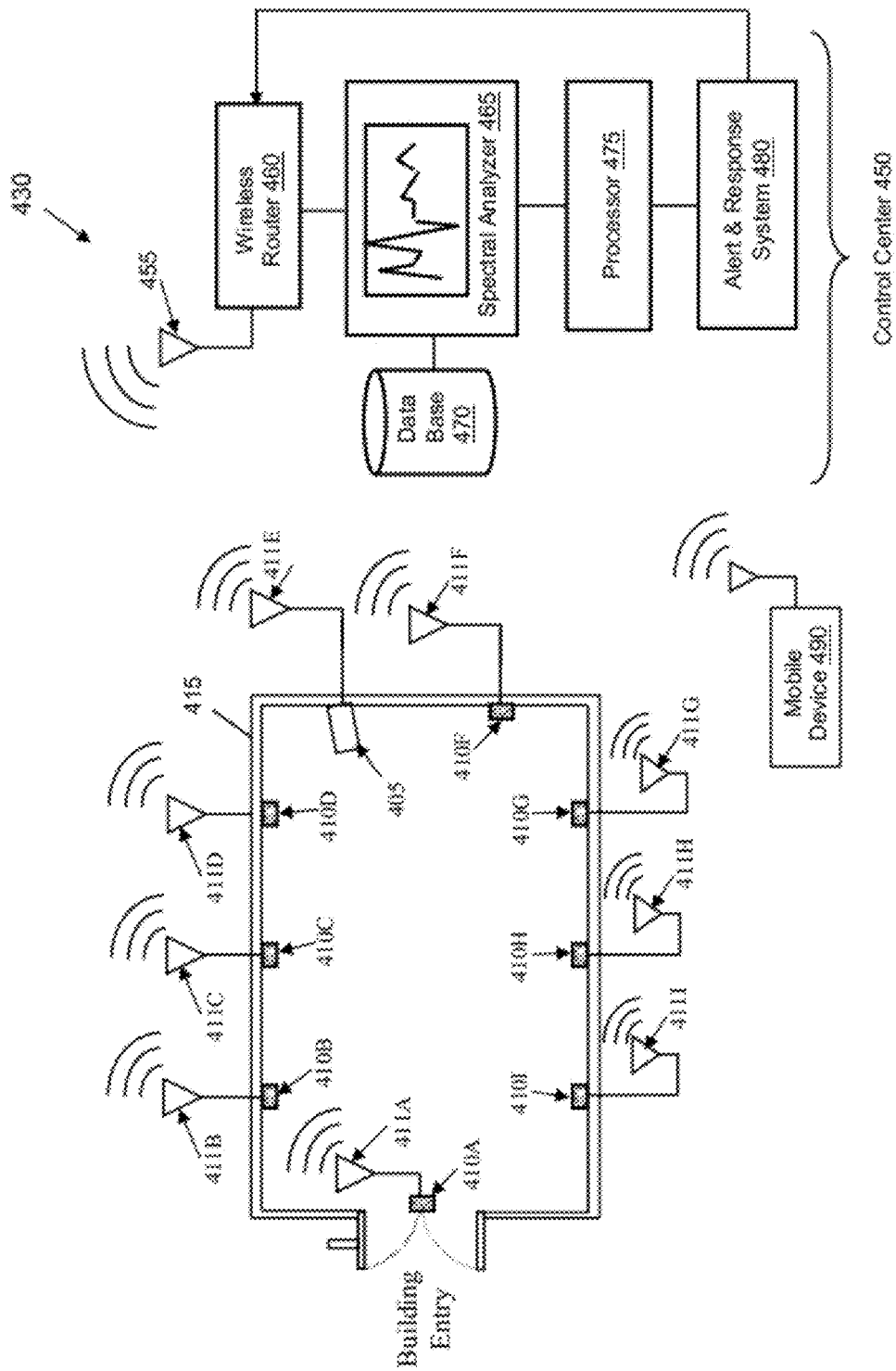
FIG. 4B is a schematic diagram for a network of wireless connected Raman scattering probes for monitoring the safety of a building.

In some embodiments, a sensor-network system 430 is shown in FIG. 4B. A building 415 includes a building entry and a plurality of walls. Probe assemblies 410A-410I are installed at various locations in the building 415. The probe assemblies 410A-410I are respectively coupled to antenna 411A-411I which can transmit locally detected spectral information to a control center 450.

Figure 4C:
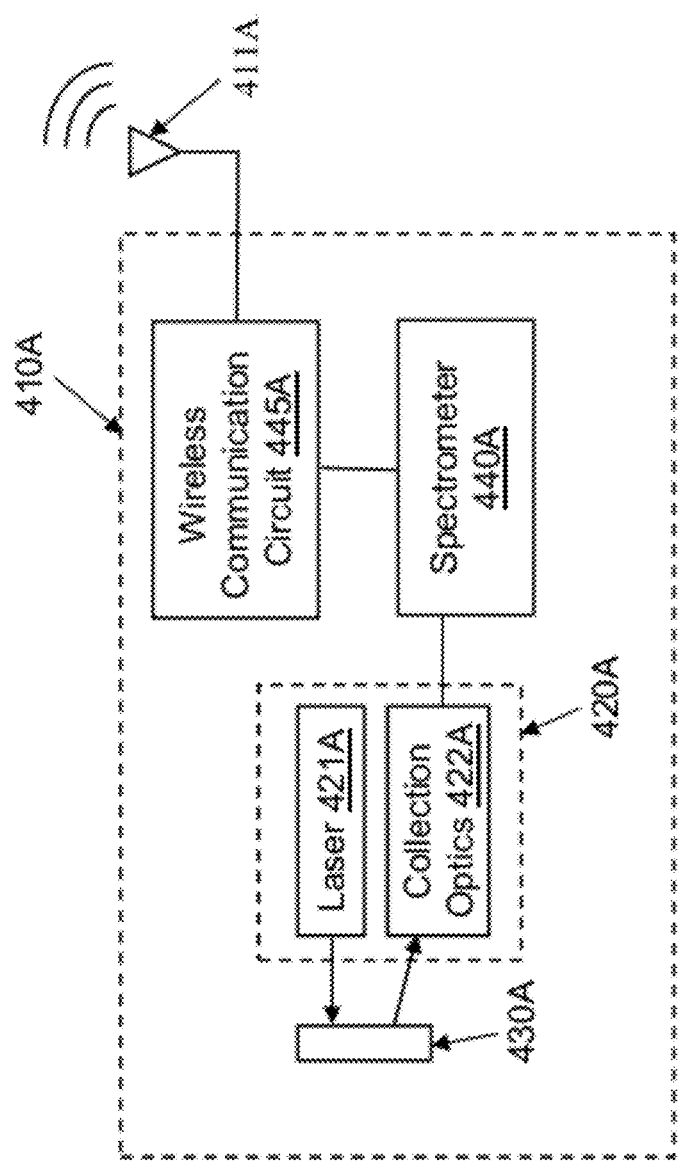
FIG. 4C illustrates an exemplified configuration for a probe assembly capable of wireless communication with a control center.

Each probe assembly 410A, as shown in FIG. 4C, includes a probe head 420A and a sensor 430A positioned adjacent to the probe head 420A. The sensor 430A can collect substances in the ambient environment. In some embodiments, the sensor 430A includes a nano-structured surface that can adsorb molecules of the substance collected in the ambient environment. The probe head 420A includes a compact laser 421A (e.g. a semiconductor laser) that is configured to illuminate a laser beam on the sample molecules in or adsorbed on the sensor 430A. The probe head 420A further includes collection optics 422A that can collect light scattered from the sample molecules in or adsorbed on the sensor 430A, wherein the scattered light comprises information about molecules of the sample molecules. The sensor 430A is compatible with the sensor 105 (FIG. 1B) that includes a nano structure on the surface. The sample molecules can be adsorbed on the nano surface structures to scatter the incident laser light. The sensor 430A can also include a liquid solution that is configured to receive sample material to be detected (e.g. see FIG. 7 below). The solution can also include nano particles configured to adsorb the molecules of the sample materials.

The probe head 420A also includes a compact spectrometer 440A that is configured to produce a spectrum of the scattered light collected by the probe head 420A. The spectral data is output from the spectrometer 440A to a wireless communication circuit 445A. The wireless communication circuit 445A can include an RF transceiver, one or more amplifiers, and impedance matching circuit. The wireless communication circuit 445A is configured to transmit the spectral data detected by probe assembly 410A to the control center 450 (FIG. 4B).

The control center 450, referring back to FIG. 4B, includes a wireless router 460 coupled with an antenna 455 configured to receive the wireless signals from the antenna 411A-411I and produce electronic signals comprising spectral data extracted from the wireless signals. The control center 450 can be located within a short range (e.g. within a couple of miles) from the source location (e.g., the building 415) to allow wireless signals comprising the spectral data to be communicated in a wireless protocol such as WiMax, WiBro, WiFi, WLAN, 802.16, and others. The control center 450 can also be located at a long distance from the source location, wherein the wireless signals comprising the spectral data can be communicated using wireless communications standards and protocols such as Global System for Mobile communications (GSM), Universal Mobile Telecommunications Service (UMTS), and Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, and Long Term Evolution (LTE). CDMA can include CDMA2000, and Ultra Mobile Broadband (UMB).

A spectral analyzer 465 at the control center 450 is configured to receive the electronic signals comprising the spectral data from the wireless router 460. A spectrum such as Raman spectrum is produced and analyzed by the spectral analyzer 465. As described in more detail below, different chemical or biological substances often carry unique spectral signatures. These spectral signatures can be predetermined using a sensor similar to the ones installed in the probe assemblies 410A-410I. The spectral signatures can be stored in a database 470. The spectral analyzer 465 can use the spectral signatures stored in the database 470 as reference to identify spectral signatures in the spectral data. A processor 475 can compute and determine substances captured by the plurality of probe assemblies 410A-410I at different times at different locations of the building 415. If a hazardous substance is identified from the spectral data obtained by one or more probe assemblies 410A-410I, the processor 470 can immediately send a report to an alert and response system 480. The hazardous substance can, for example, include explosives and flammable materials, poisonous gas and other harmful chemicals, and contagious virus and bacteria. The alert and response system 480 is configured to send warning notification signal to the wireless router 460, which can in turn transmit wireless signals to mobile devices 490 and other wireless devices to alert security and other responsible personnel to take proper response actions. The mobile device 490 can include a laptop personal computer, a personal digital assistant (PDA), a mobile internet device (MID), a cellular phone, a smart phone, or a wireless server or router.

Figure 4D:
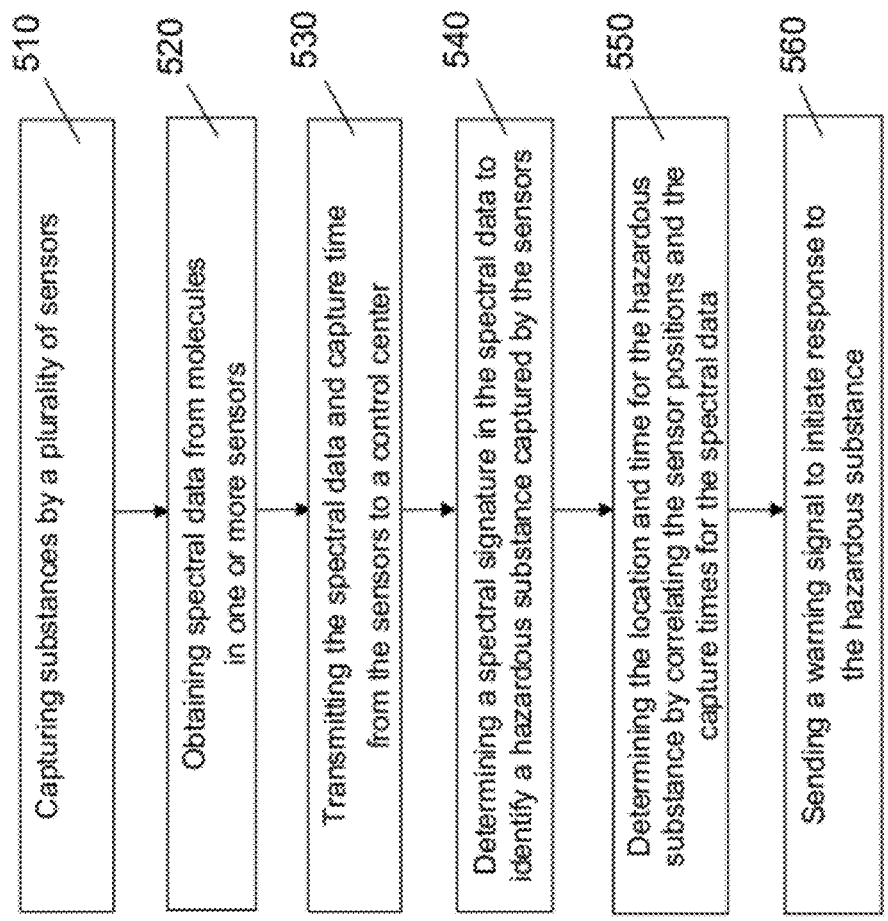
FIG. 4D is an exemplified flowchart for identifying the time and location of the source of a hazardous substance.

In some embodiments, referring to FIG. 4D, a network of probe assemblies are installed at predetermined positions in a building, an airport, a custom, a conveyance system for cargo or luggage, a doctor a health advisor's office, a check station on a road, a harbor, in a vehicle, a ship, a submarine, an airplane, a train, a subway, an industrial site, a resort area, a shopping mall, a research Lab, a school, or a water source, etc., as described above in relation to FIGS. 3B-4C. Each probe assembly includes a sensor and a probe head configured to emit a laser beam and collect scattered light from the molecules in the sensor. The sensor can have a nano structured surface configured to adsorb the molecules. The probe assembly also includes a spectrometer for producing spectral data such as Raman spectrum from the scattered light. The network of sensors can periodically capture substances (step 510) from each sensor's environment. For sensors having nano-structured surfaces, molecules of the captured substance are adsorbed on the nano structured surfaces on the sensors. Spectral data are next obtained from the molecules adsorbed to the nano structured surfaces in one or more sensors (step 520). Alternately, the molecules to be detected can be captured in a sample solution, and/or adsorbed to nano particles suspended in the sample solution. As described above, a laser beam is emitted by a laser in the probe assembly to illuminate the molecules adsorbed on the nano structured surfaces on a sensor or in a sample solution. Light scattered by the molecules is collected by the probe assembly. The spectral data is obtained from the scattered light by a spectrometer in the probe assembly. An example for the spectral data is Raman spectrum. The nano structured surface on the sensor provides surface enhancement to the signal intensity in the Raman spectrum. The substance capture and associated spectral data can be periodically conducted, for example, at 1 min, 10 min, 15 min, or hours of intervals. In some embodiments, spectral data can be produced in response to a command received from a control center.

The spectral data is next transmitted from the sensors to a control center (step 530). The substance capture time can also be transmitted in conjunction with the spectral data. The spectral data transmission can be via a wired data lines (as shown in FIG. 4A) or a wireless communication network (as shown in FIGS. 4B and 4C). The data center can include a spectral analyzer and a data base storing spectral signatures of predetermined know hazardous substances. The spectral analyzer is used to determine if a spectral signature exists in the spectral data received from the sensors. A hazardous substance can be identified if a spectral signature for a known hazardous substance is found in the spectral data (step 540).

The hazardous substance may be identified by more than one sensor in the network of sensors. The identifications of the hazardous substance can occur at different times by different sensors. For example, as a passenger 200-2 walks through the passageway 210 (FIG. 3A), different sensors in the network may pick up the hazardous material at different times and at different location. A processor (475, FIG. 4B) at the control center can determine the location and time for the hazardous substance by correlating the sensor positions and the capture times for the spectral data (step 550). The location for a stationary hazardous material can be determined by interpolating the positions of the sensors. The location dependence of the hazardous substance detected at different sensors can be used as weighting factors to determine the exact location of the hazardous material, which can be expressed in a two-dimensional (2D) coordinate or a three-dimensional (3D) coordinate. The capture times of the hazardous substance by different sensors at different locations can be used by the processor at the control center to determine a spatial-time profile (that is locations as a function of time) for the hazardous material. The position of the future locations of the hazardous can therefore be predicted by the processor.

In some embodiments, the spectral data collected by the sensors can be used in conjunction with image data captured from the scene near the spectral sensors. For example, a video camera 405 at a location near the spectral sensor where the hazardous substance is identified can capture a suspected person or package. The image of the suspected person or package can be stored and reported in association of the location of the hazardous substance to prepare for an appropriate response.

A warning signal is next sent to an alert response system which can initiate response to the hazardous substance (step 560). The warning signal can be in the form of emails, text messages, and voice phone call, etc. The level of urgency can be categorized by different risk levels such as green (safe), blue, yellow, orange, red (the most risky). The warning signal can include the current and/or anticipated position of the hazardous substance as well as the suspected exterior appearance for the carrier or the package for the hazardous substance. Appropriate personnel can be alerted. Security personnel can be dispatched to the location of the hazardous substance. An evacuation can be initiated.

Figure 5:
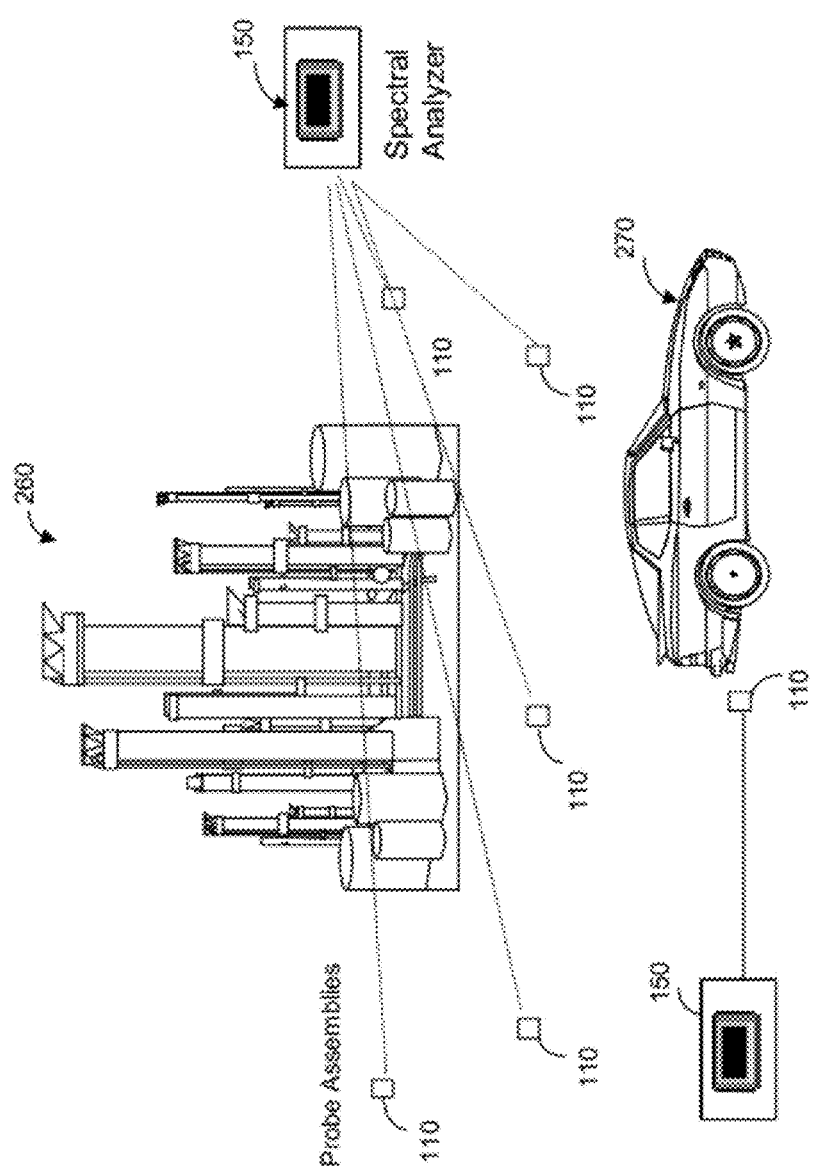
FIG. 5 is a schematic diagram showing environmental monitoring using a Raman scattering probe.

FIG. 5 is schematic diagram of applying the disclosed sensors to monitor harmful chemicals released into the environment. The probe assemblies 110 are distributed around potential pollution source, e.g., a factory 260 or around highway where great number of automobiles 270 pass through. The probes assemblies 110 can be distributed around the monitored areas and transmit scattered light to a central spectrum analyzer 150, which can determine the contents and concentration of substance released into the environment. The monitoring sample can be, but not limited, soil, water, lake, river, seashore, well, plants, etc. This application can be extended to car exhausted gas detection and monitoring by placing the probe assembly near by car exhausting output.

Exemplified Applications

In some embodiments, compact Raman sensor having wireless communication capability can be used inside human body. For example, a system-on-chip Raman system can be made in a tablet size which includes on-chip mini-laser source, MEMS based mini-spectrometer, wireless module, mini-probe, etc. One exemplified application is disease diagnosis of digest system. For example, a patient can swallow a tablet sized Raman system after his/her digest system got cleaned (similar procedure to that of preparation for colon endoscopy test). Raman scans are to be taken at predetermined time intervals. The spectral data is then transferred by wireless module to a wireless receiver outside of the human body. A computer can analyze the spectral data by searching and matching existing data in a data base, which can lead to identification of a disease. In another exemplified application, a needle-shaped minimally invasive probe head can bring mini-Raman sensor into diagnosis area inside a human body. Raman spectral data can be transferred through optic fiber, or wireless module. Such applications can include but not limit to diagnosis of cancers (such as breast cancer, colon cancer, esophageal cancer, lung cancer, liver cancer, bladder cancer, and stomach cancer), Alzheimer's disease, Parkinson disease, etc.

The disclosed Raman spectral sensing systems and methods are suitable for biotechnology and biomedical applications, such as biometric identity verification by testing samples of tissues or body fluids of a human or an animal, A549 cell of lung cancer, DNA, RNA and proteins, and bio-markers include CEA, CA-125, CA 19-9, PSA, AFP, A549, DNA sequencing, DNA sorting, etc.

The disclosed Raman spectral sensing systems and methods are suitable for drug screening. The samples for drug screening can be obtained by human body fluid test, or/and breath test. The disclosed Raman spectral sensing systems and methods are also suitable for forensic applications. The samples can be in the forms of saliva, urine, and powders. Related applications also include false signature recognition; human identification and screening by DNA profiling; identify microscopic paint fragments, fiber identification, etc.

The disclosed Raman spectral sensing systems and methods are suitable for security applications such as detections of hazardous materials, chemical weapons, biological agents, explosive materials (in the forms of powders, solids, and liquids), flammable materials including liquids, solids and powders, narcotic drugs, and radioactive materials.

The disclosed Raman spectral sensing systems and methods are suitable for food safety inspection and environmental monitoring. Harmful chemicals in the forms of gas, liquid, powder, gel, aerosol, or solid phases can be monitored in food, fruits, beverages and water. The harmful chemicals can include residue pesticides (e.g., methamidophos, cypermethrin, deltamethrin, malachite green, etc.), dioxins, illegal artificial additives (e.g., sudan I, sudan II, sudan III, sudan IV, melamine, rhodanmine B, sulfide (e.g., NaS), art green, etc.), heavy metals in water including but not limited to Pd, Cd Hg, As, Cr, cyanides (e.g., KCN, NaCN), chlorates, sulfates. Food processing by-products (e.g., acrylamide formed from potato chips from processing temperature over 120° C. can be monitored to detect harmful chemicals such as acrylamide using the disclosed Raman spectral sensing techniques. Foods wider investigation include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc.

The disclosed Raman spectral sensing systems and methods are suitable for identifying and monitoring food packaging processing and preparation materials, which includes identifying and screening polyvinyl chloride (PVC) and phthalate materials used as the microwave food wrap, kitchen film, food packaging, food and liquid container, and processing and preparation materials.

The disclosed Raman spectral sensing systems and methods are suitable for identifying counterfeit merchandizes such as medicines, drugs, milk-based powders, edible oil, wines, gemstones, currency bills, false signature through inks, art pieces, gasoline, etc.

The disclosed Raman spectral sensing systems and methods are suitable for industrial quality control and production safety monitoring. Application areas can include process control for product quality, process and production safety at gas and wet chemical process lines, which can include petroleum refinery plant, chemical engineering manufacturing plant, semiconductor wet chemical process line in clean room, airline and space shuttle, boat, ship and submarine, etc.

The disclosed Raman spectral sensing systems and sensor networks can be applied to medical clinic offices, surgery operation rooms, shopping centers, resort area, buildings, customs, road check station, harbors, airports, vehicles, boats, ship, airplanes, space shuttles, industrial process sites, R&D research labs, quality control offices, education institutes, labs offices, and water sources such as surface water, wells, ground waters, and so on.

Figure 6A:
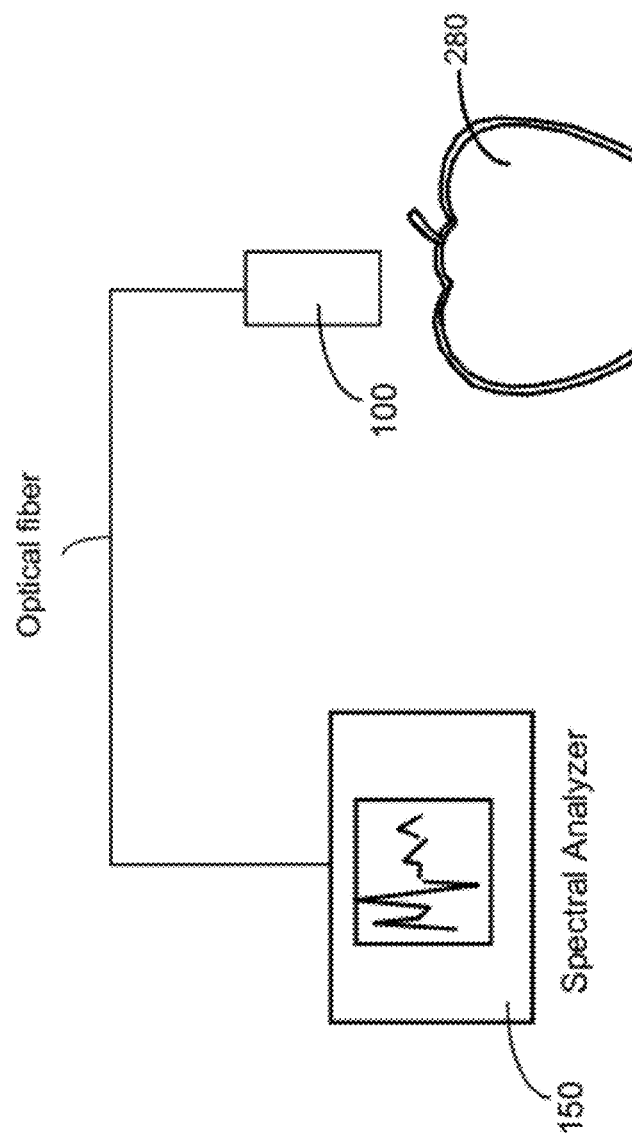
FIG. 6A is a schematic diagram showing inspection of food safety using a Raman scattering probe.

FIG. 6A is schematic diagram of applying the technology of Surface-Enhance

Raman Scattering using a sensor to monitor substances for inspecting quality and safety of foods. A light scattering probe 100 is placed close to a food item 280, i.e., an apple or different fruits, vegetables or other food items that could be contaminated through transportations, food processing, or even food growth process. The molecules of residue pesticide or other contaminations are drawn into the light scattering probe 100. A sensor is used to detect any suspect harmful chemicals contained in the food.

Figure 6B:
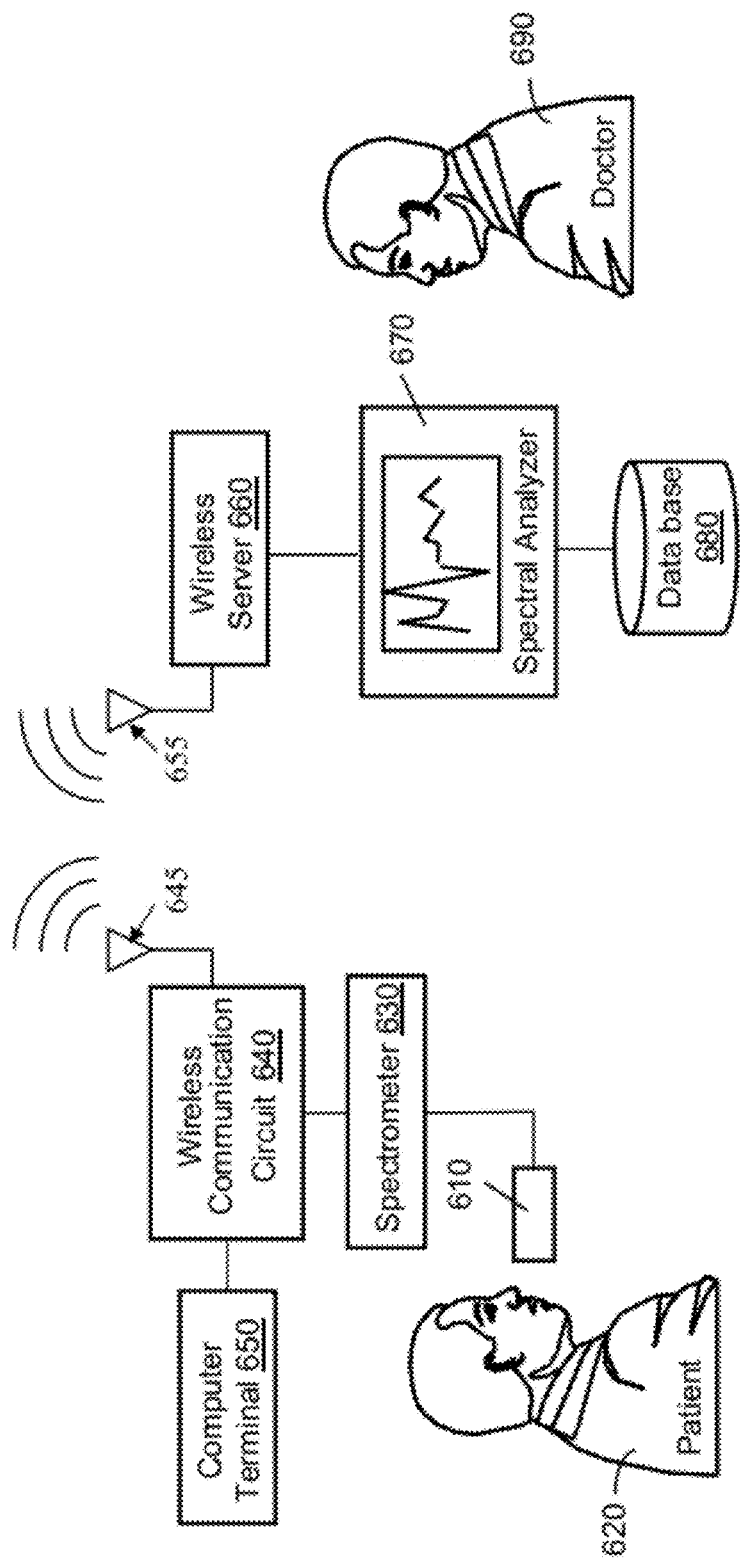
FIG. 6B illustrates an exemplified system for remote disease diagnosis and biomedical detection using a Raman scattering probe.

FIG. 6B shows an application of disclosed Raman spectral technique to monitor substances for early decease detection and diagnosis. A doctor can remotely monitor and diagnose many patients at homes and hospitals. The probe assembly 610 is placed near a patient 620 for carrying out a physical examination, a check-up from recuperation from a sickness, or for disease diagnosis. Human breathed air can carry special chemicals such as alkenes and benzene derivatives. if a person under screening has a disease such as cancers including but not limited to lung cancer, breast cancer, liver cancer, pancreas cancer, ovarian cancer, etc. Raman sensing technology is able to fingerprint those chemicals in breath test to identify some special diseases such as cancers. The patient blows the outpoured breath-air to the probe assembly 610. The sensor in probe assembly receives the inlet air for generating a scattered light corresponding to the molecules contained in the airflow from a patient or a breath air sample provider. Spectral data of the scattered light is produced by a spectrometer 630. A wireless communication circuit 640 can convert the spectral data into an RF signals which can be transmitted in a wireless signal by an antenna 645. The wireless signal can also include information (e.g. patient's name, identification, etc.) about the patient 620. A computer terminal 650 coupled to the wireless communication circuit 640 can display information received from a doctor's office and allows the patient to input information to be transmitted to the doctor's office.

An antenna 655 at a doctor or a health advisor's office receives the wireless signal or wireless signal from a plurality of patients at a distance. A wireless server 660 can down convert the wireless signal and extract the spectral data and other information about the patient or input by the patient. The spectral data is analyzed by a spectral analyzer 670 using spectral signatures stored in a data base 680. The spectral signatures can indicate a plurality of predetermined diseases. The determination of a spectral signal in the spectral data may indicate the patient is carrying the associated disease or has not fully recovered from a previously diagnosed sickness. The signal strength can indicate the severity of the disease suffered by the patient. A doctor 690 can also make a determination about the nature and severity of the disease by visually inspecting the spectral data. The described systems and methods are suitable for early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually or automatically, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a sensor to enhance the sensitivity and intensity of Raman scattering detections. The disclosed trace chemical detection using Raman light scattering can also be applied to other areas, including but not limited to identify Alzheimer's disease, Parkinson disease, non-invasively test glucose to monitor diabetes, non-invasive test and evaluate level of carotenoids to monitor antioxidant status for early cancer screening purpose, and so on.

Figure 6C:
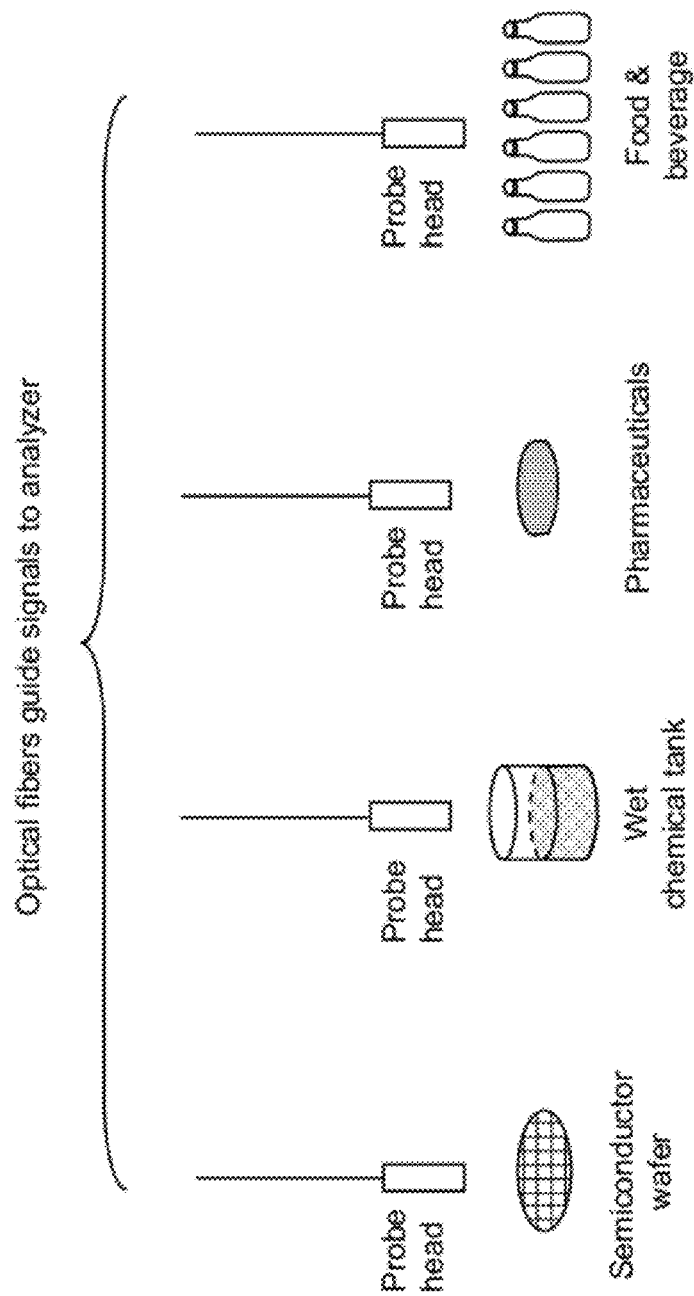
FIG. 6C is a schematic diagram showing manufacture quality control using a multi-channel sensing system.

FIG. 6C is schematic diagram of Raman scattering application in industrial quality control. The applications can include in-line monitoring of chemical concentrations in a plurality of wet chemical process line, stand-off monitoring of sealed chemical tanks, remote trace chemical detection, semiconductor wafer defect evaluation, and monitoring of the food, fruit and vegetable storage, etc. The spectral signals collected by probe heads at a plurality locations can be fed by optical fibers in multiple channels to an spectral analyzer at a central office, wherein the spectral data are analyzed. The spectral signatures in the spectral data can lead to identify harmful substances in the food, etc.

FIG. 6D is schematic diagram of a multi-channel Raman scattering sensing system that can identify and screen materials for counterfeit merchandise and food safety screening. The applications may include operations such as food, drug and medicine screening, which may or may not involve a nano technology module in a sensor. The excitation laser beams in the probe heads can directly impinge on samples under test. The scattering light from the tested materials are collected by the probe heads. The Raman spectra of the scattered lights show spectral signatures that can provide indications whether there are illegal additives added to the commercial merchandises. The potential counterfeit merchandise such as milk-based powder, wine, and medical tablets may be placed under the Raman detector as materials under investigation and screen. The spectral signals can be collected from different samples and fed by optical fibers in multiple channels to a spectral analyzer at a central office, wherein the spectral data are analyzed. The applications can be extended to authenticated signatures and currency bills by detecting false signature and false bills by generating Raman scattering spectrum of the signature and dollar bills and compare these spectrum with measurements obtained from authenticated signature and dollar bills.

Figure 7:
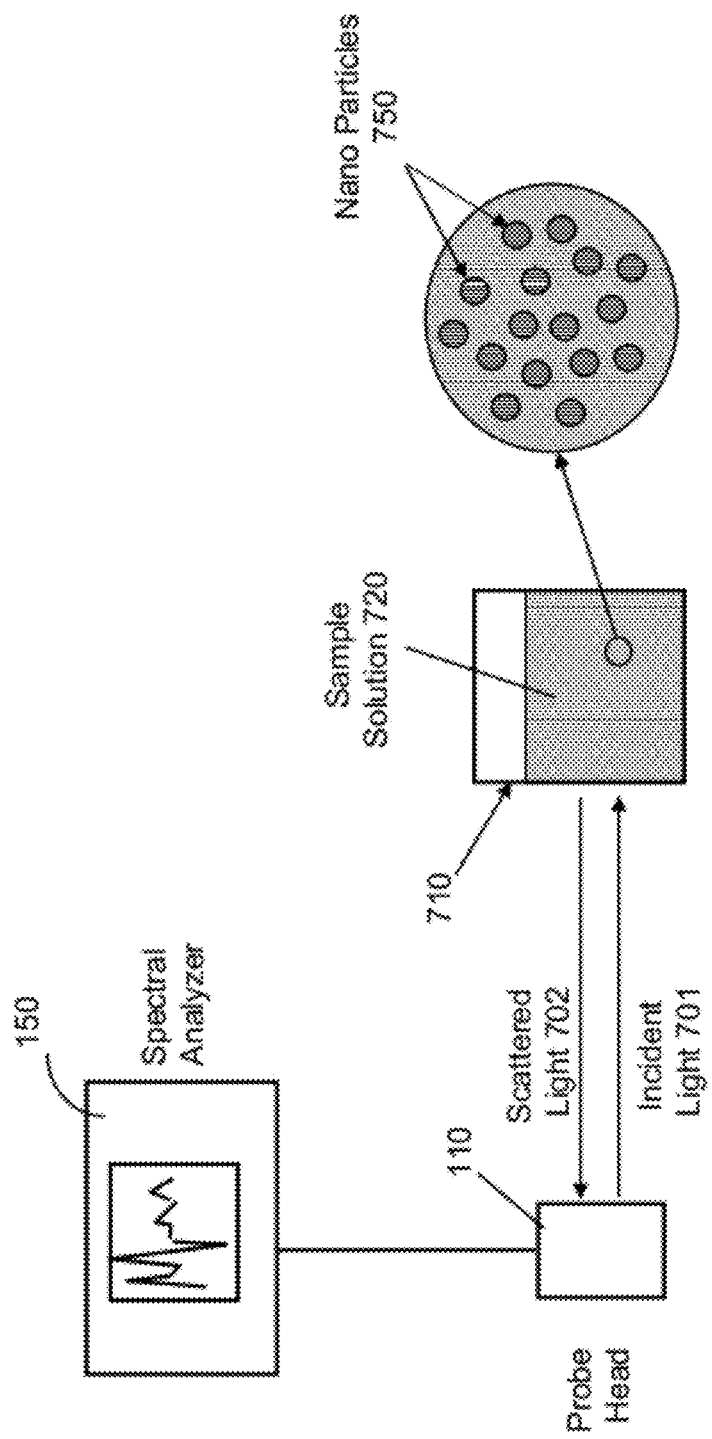
FIG. 7 is a schematic diagram showing a configuration for detecting trace chemical or biological substance using a solution containing nano particles and a light scattering probe.
Figure 8:
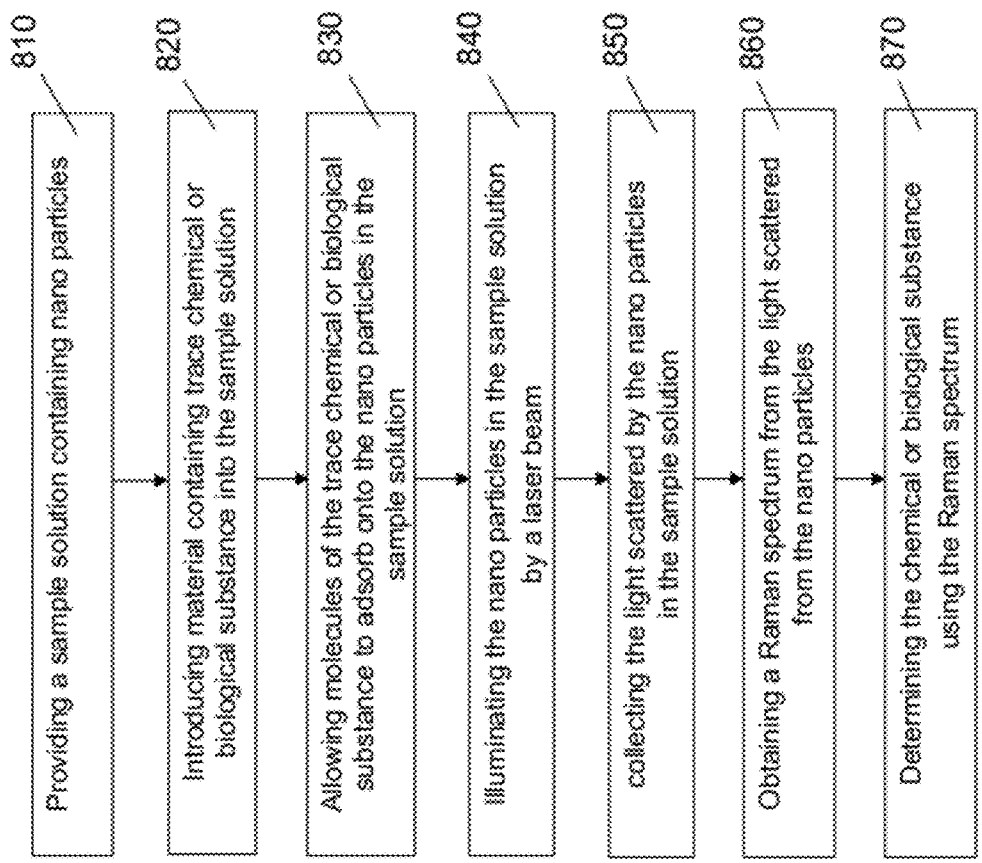
FIG. 8 is flow diagram for detecting trace chemical or biological substance using a solution containing nano particles and a light scattering probe.

In some embodiments, referring to FIGS. 7 and 8, a sample solution 720 is introduced into a container 710 (step 810). The container 710 can be an optical vial, a beaker, or a transparent test tube, etc. The sample solution 720 also contains nano particles 750 or carbon nano tubes. The nano particles 750 can exist in the form of a colloidal suspension in the sample solution 720. A sample material containing the chemical or biological substance is introduced into the sample solution 720 (step 820). The sample material can exist in a solid, a liquid, an aerosol, a sol gel, or a gas form. The sample material is dissolved in the sample solution 720 to allow molecules of the chemical or biological substance to adsorb on surfaces of the nano particles 750 (step 830). A probe head 110 (shown in FIG. 1A) emits an incident light 701 (such as a laser beam) to illuminate the nano particles 750 and the chemical or biological substance in the sample solution 720 (step 840). Scattered light 702 from the nano particles 750 and the chemical or biological substance is collected by the probe head 110 (shown in FIG. 1A) (step 850). The output signal from the probe assembly is analyzed by the spectral analyzer 150. As shown in more detail in the examples below, a Raman spectrum is obtained from the scattered light (step 860). Spectral signature(s) in the Raman spectrum can be used to determine the trace chemical or biological substance adsorbed to the nano particles (step 870).

In one aspect of the present disclosure, material compositions of the nano particles 750 in the sample solution 720 are prepared to enhance the intensity of the scattered light 702 and Raman spectral signal from the nano particles. For example, the nano particles 750 include metallic materials such as Al, Ag, Au, Cu, Fe, Co, Ni, Cr, Zn, Sn, Pd, Pt, and their alloys, oxide materials such as titanium oxide, silicon oxide, zinc oxide, etc, silicon, and polymeric materials. The nano particles 750 can be charged in the sample solution 720 to assist the separation between the nano particles and the formation of a colloidal suspension. The nano particles 750 can also include polymers tethered to the particle surfaces to help repel each other in the sample solution 750.

In some embodiments, the nano particles 750 can include carbon nano tubes. The diameters of the carbon nano tubes can be from 0.3 nm to 100 nm. Their lengths can be from 5 nm to multiple millimeters. The length-to-diameter ratio of the carbon nano tubes can be as high as 50 million. The carbon nano tubes can have single-walls or multiple walls. The carbon nano tubes can be in the form of Fullerite, a torus, nanobuds, and nanoflowers.

In the presently disclosed systems and methods, when the carbon nano tubes can be placed the sample solution 720 to form a suspension of nano particles in which the sample material is added. The carbon nano tubes can also be introduced on a substantially flat surface or a surface already formed with nano structures. A sample material is then introduced to such a surface containing the nano carbon tubes. In either cases, a light optical beam (such as a laser beam) is directed to illuminate the nano carbon tubes and the sample material. Enhanced localized electro-magnetic filed can assist charge transfer between molecules of the targeted chemical or biological substances, which results in enhanced Raman spectral signal.

In another aspect of the present disclosure, the nano particles 750 can be made of a magnetic or ferromagnetic material such as Iron (Fe), Cobalt (Co), and Nickel (Ni), or Fe, Co Ni contained compounds, such as alloy or oxide of Fe, Co, Ni, which can enhance the Raman spectral signal by applying an electrical field, a magnetic field, or an electro-magnetic field to the sample solution 750. The electrical field, the magnetic field, or the electro-magnetic field can be static or alternating.

In another aspect of the present disclosure, the sample solution 720 can include a mixture of nano particles of different material compositions. For example, the nano particles can include a mixture of silicon nano or micro-particles and metallic nano particles, or a mixture of silicon nano or micro-particles and polymeric nano particles, or a mixture of silicon nano or micro-particles, metallic nano particle, metallic oxide nano particles, and polymeric nano particles. Raman signal intensity can be enhanced by mixture compositions.

In another aspect of the present disclosure, the solvent in the sample solution 720 is also designed to enhance the light scattering intensity from the nano particles. It was found that ions and especially multi-valence ions can significantly enhance the signal intensity of the Raman signal. An ionic material can thus be added to the sample solution 720. Examples of ions that the ionic material carries to the sample solution 720 can include $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, and $I^-$, and so on. The ions can have mono charge or preferably double or high charges in the sample solution 720. The ions can have positive or negative charges. The sample solution 720 can have an ionic compound, including but not limited to LiF, NaF, NaCl, KCl, KI, etc. The ionic concentration can be in a range from 10 µM to saturated level.

Figure 9A:
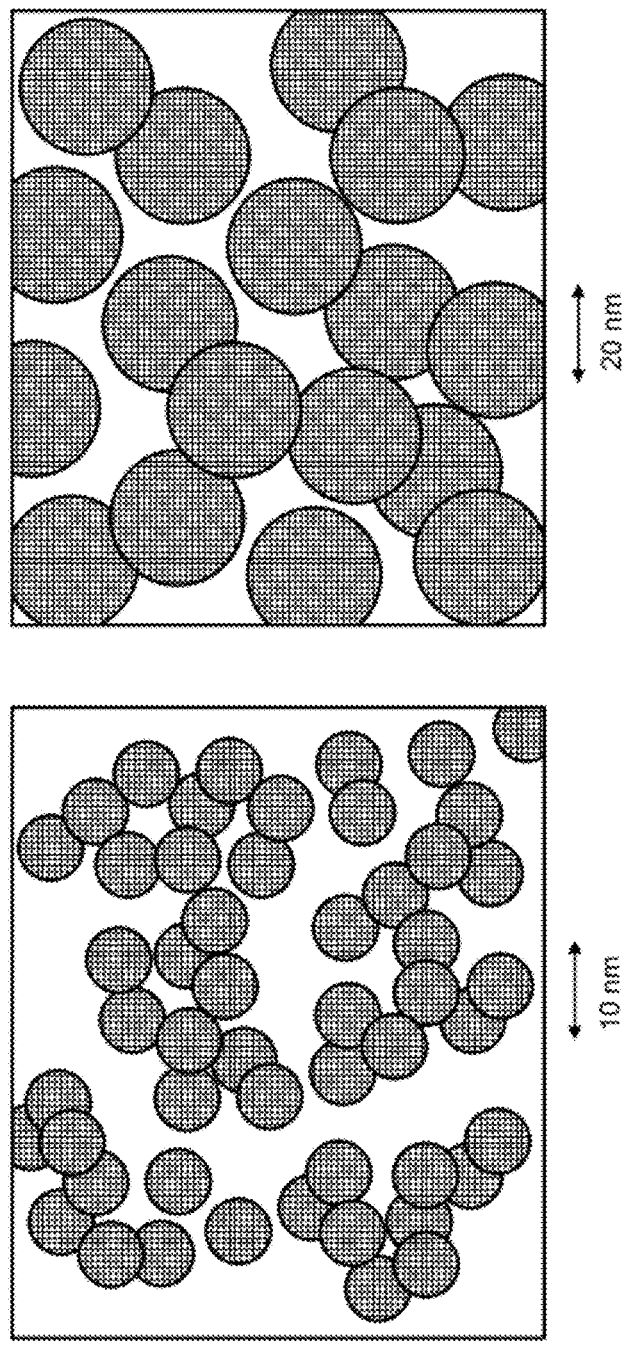
FIG. 9A is an exemplified micrograph of the nano particles shown in FIG. 7 using scanning electron microscope.
Figure 9B:
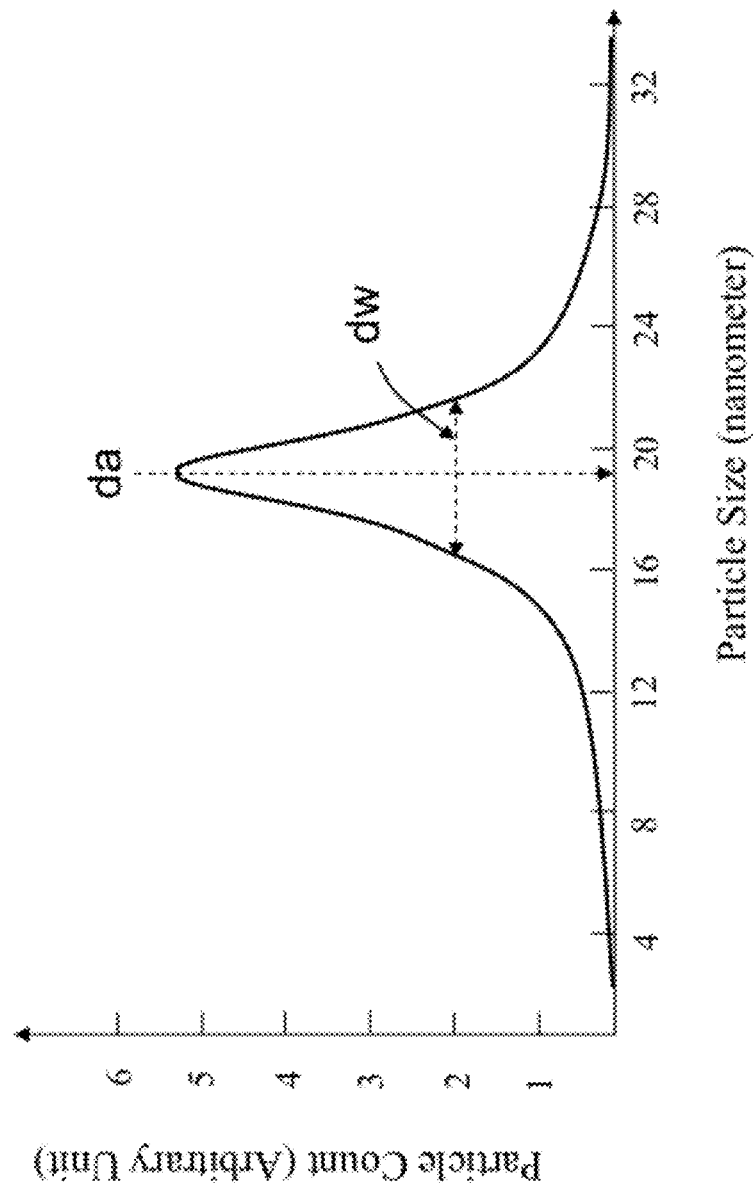
FIG. 9B is an exemplified size distribution of the nano particles in the solution shown in FIG. 7.

The nano particles 750, as shown in FIG. 9A, can exist in round or irregular shapes. The nano particles can be individually separated and have also group in clusters in the sample solution 720. The nano particles 750 can have a size distribution, as shown in FIG. 9B, which is characterized by an average particle dimension da and a particle-dimension distribution width $d_w$ for the particle size distribution. The average particle dimension $d_a$ can range from about 1 nm to about 10,000 nm, or from 2 nm to 500 nm. The ratio $d_w/d_a$ can range from about 0.01 to about 3, which defines a quite monodispersed distribution to a polydispersed particle distribution. The ratio $d_w/d_a$ can often range from about 0.03 to about 1.

In some embodiments, a sample solution can include nano particles and a sample material that can include micro-sliced tumor tissue. The temperature of the sample solution can be controlled within a predetermined small range by a TE cooler and heater with temperature variation is smaller than 1 or 2° C. The temperature range can be from −18° C. to 60° C., or from 0° C. to 40° C. The sample solution is dried on a substrate surface leaving the nano particles and the sample material on the substrate surface. A last light beam is illuminated on the nano particles and the sample material. The light scattered by the sample material with the nano particles is collected. A Raman spectrum is obtained from the scattered light. Chemical or biological substance in the sample material can be identified using spectral signatures in the Raman spectrum.

In some embodiments, substance containing the trace chemical or biological substance can be introduced onto the surface of a chemical sensor, as shown in FIG. 1, from which an incident light can be scattered and a Raman spectrum can be obtained from material determination. FIGS. 10 to 15 show a series of processing steps for fabricating a nanostructured noble metal surface on the chemical sensor (or sensor 105 in FIG. 1). A multi-layer structure 302 (FIG. 10) includes a substrate 305, a conductive layer 310, and an aluminum oxide layer 315. The substrate 305 can for example be n-type silicon flat wafer (3-8 Ω-cm) or oxidized (30-50 nm $SiO_2$) p-type silicon (5-10 mΩ-cm). The conductive layer 310 can include Ti and Ni and is deposited on the substrate 305 and can be electrically and thermally conductive. The thickness of the conductive layer 310 can be optimized to provide i) adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of the conductive layer 310 can be generally controlled in the range of 100 Å-100,000 Å, typically in the range of 100 Å-1,000 Å.

The aluminum layer 315 is deposited on the conductive layer 310. The aluminum layer 315 can have a purity of 99.999% and thickness in the range of 1.0-10.0 µm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
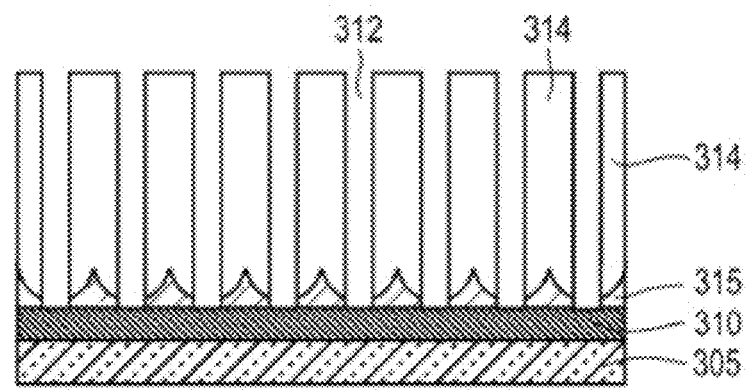
FIG. 13 is a cross-sectional view of the nano-structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
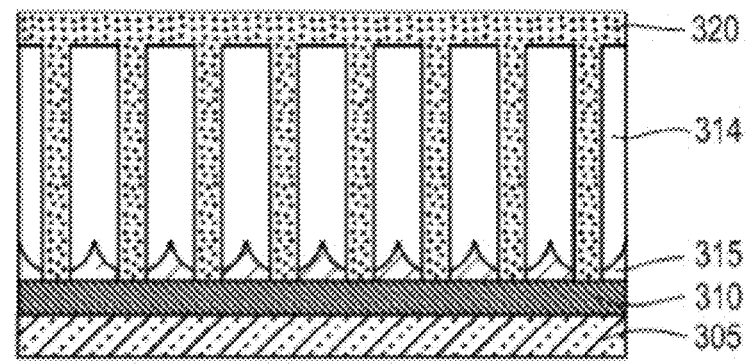
FIG. 14A is a cross-sectional view of the nano-structure formed on the multi-layer layer structure after the deposition of a noble metal.
Figure 14B:
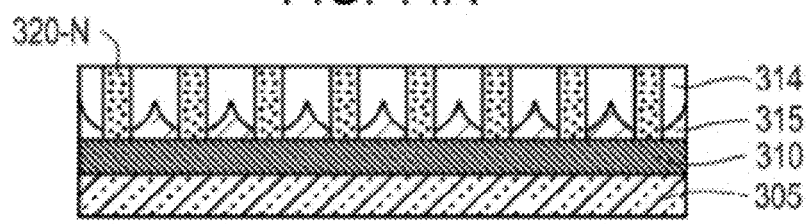
FIG. 14B is a cross-sectional view of the nano-structure formed on the multi-layer layer structure after the removal of the noble metal on the top layer.
Figure 15:
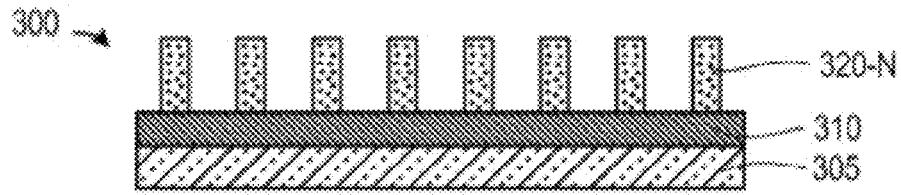
FIG. 15 is a cross-sectional view of the nano-structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 Ω-cm) or oxidized (30-50 nm $SiO_2$) p-type silicon flat wafers (5-10 mΩ-cm). The thickness of this conductive metal layer 335 can be controlled in the range of 100 Å-1,000 Å. An adhesion layer (e.g. made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection.

Figure 16A:
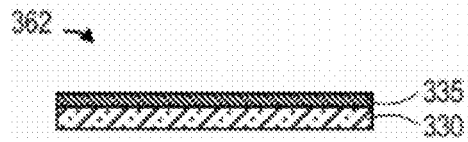
FIGS. 16A-16D, 16G, and 16H are cross-sectional views of the nano-structure formed on the multi-layer layer structure after the fabrication process.
Figure 16D:
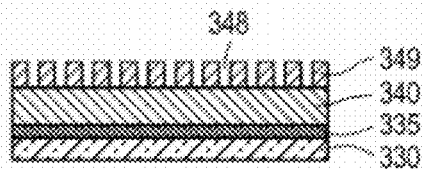
Figure 16B:

In FIG. 16B, a noble metal layer 340 is deposited on top of the conductive layer 335. The noble metal may be a silver layer, e.g., Ag layer having a thickness of 1 nm-200 nm. In FIG. 16C, a second metal layer 345 is deposited on top of the noble metal layer 340. The second metal layer 345 can include aluminum with a purity level of approximately 99.999% and a thickness in the range of 1.0-10.0 μm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340. Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-holes 348 surrounded by wall 349. Alternatively, the etching of the pores 348 can widen the pores 348 so much such they touch each other, which can produce a hexagonal array of quasi-triangle nano columns 349'.

Figure 16G:
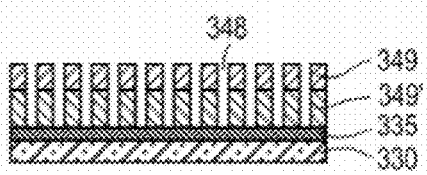
Figure 16C:
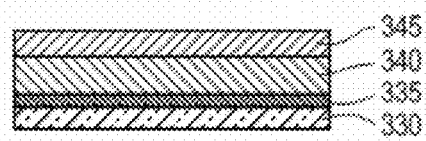
Figure 16H:
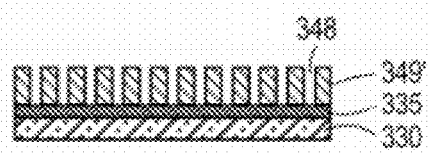
Figure 16F:
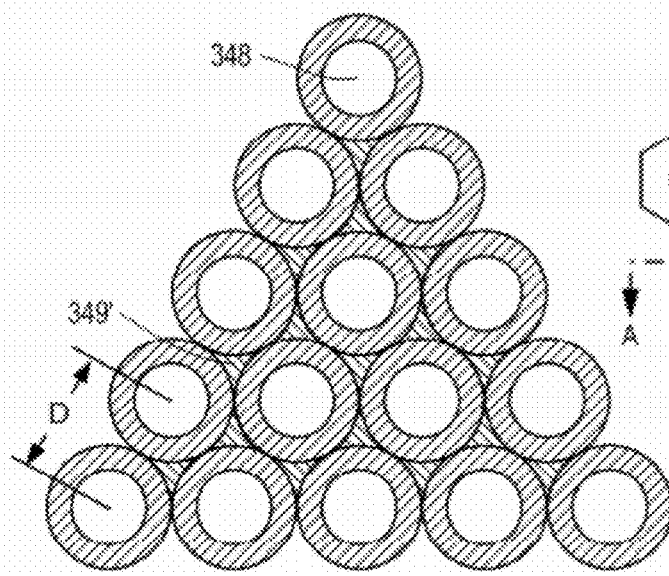
FIGS. 16E and 16F are top views of the nano-structure formed on the multi-layer layer structure after the fabrication process.
Figure 16E:
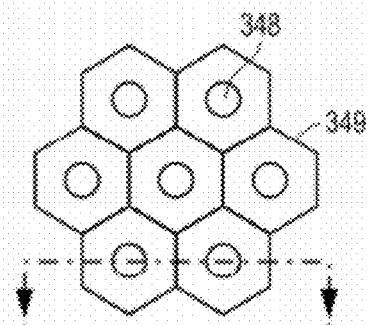

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

In some embodiments, a sensor compatible with FIGS. 1A and 1C can be prepared by introducing nano particles as described above on a structured or substantially unstructured (i.e. flat) substrate, or a sample solution. The trace chemical or biological substance can first be mixed with the nano particles in a solution to allow molecules of the trace chemical or biological substance to be adsorbed onto the nano particles. The sample solution containing the nano particles are then introduced onto the structured or unstructured surface of the chemical sensor. In other words, nano surface structures can be prepared by coating the surface of the sensor 105 by a solution containing a colloidal suspension of nano particles. The nano particles can be formed by a metallic materials (such as Al, Ag, Au, Cu, Fe, Co, Ni, Cr, Zn, Sn, Pd, Pt, and their alloys), oxide material (such as titanium oxide, silicon oxide, zinc oxide, etc), or a polymeric material. Oxide or polymeric particles can be doped with metal ions or coated with a conductive material. The colloidal suspension can include single nano particles or clusters of nano particles. A nano surface structure is formed after the solution applied to the sensor surface. The solution can evaporate, leaving the nano particles adsorbed with the target molecules on the sensor surface.

In some embodiments, diseases can be identified by analyzing Raman spectra obtained from body fluids from a patient using the light scattering probe 100 as described above in relation to FIGS. 1A-2, 6B, 7-9B. A body fluid obtained from an individual person can be directly introduced onto a sensor (105 in FIG. 1A) or mixed with a sample solution (720 in FIG. 7) containing nano particles. Light scattering and Raman spectral analyses can be conducted as shown in FIGS. 1A-1C or in FIG. 7. Alternatively, the sample solution containing the nano particles can be introduced on a structured or unstructured surface of a sensor, as described above, which is used in subsequent light scattering and Raman spectral analysis.

Figure 17:
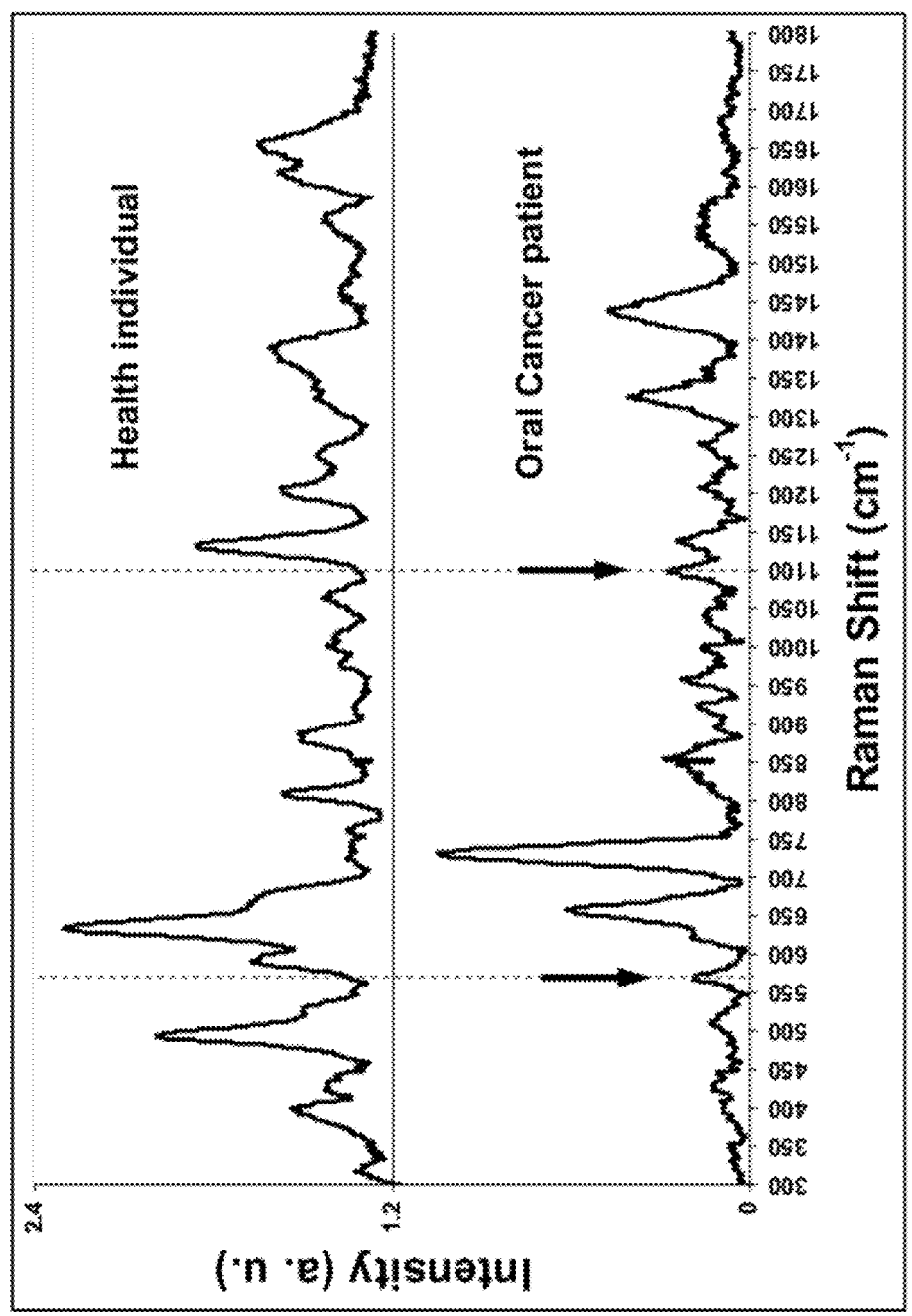
FIG. 17 illustrates an exemplified Raman spectral signature for oral cancer detected in the saliva of an oral cancer patient by the disclosed Raman scattering probe.

Referring to FIG. 17, the Raman spectrum obtained from a saliva sample from an oral cancer patent has show two signature spectral peaks respectively around, for example, 560 $cm^{-1}$ (in the region from 530 $cm^{-1}$ to 570 $cm^{-1}$) and 1100 $cm^{-1}$ (in the region from 1185 $cm^{-1}$ to 1105 $cm^{-1}$) which are absent in a healthy individual without the oral cancer. The signature spectral peaks around 560 $cm^{-1}$ and 1100 $cm^{-1}$ are associated with molecular vibrations for C—S, S—S, O—P—O(PO$_2$), C—N, or C—C bonds in, for example, cysteine, ATP, ADP, DNA, RNA, proteins, and other phosphate containing biological compounds. The identification of these spectral signatures can include the steps: a spectral band is first selected at Raman peaks with Raman shift in unit of cm$^{-1}$ (wave number) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed as likely having oral cancer or at an early stage of an oral cancer if spectral signatures around 560 cm$^{-1}$ and 1100 cm$^{-1}$ are both identified. Appropriate doctors and patients themselves may be alerted for further testing using the same or other types of diagnosis techniques.

Figure 18:
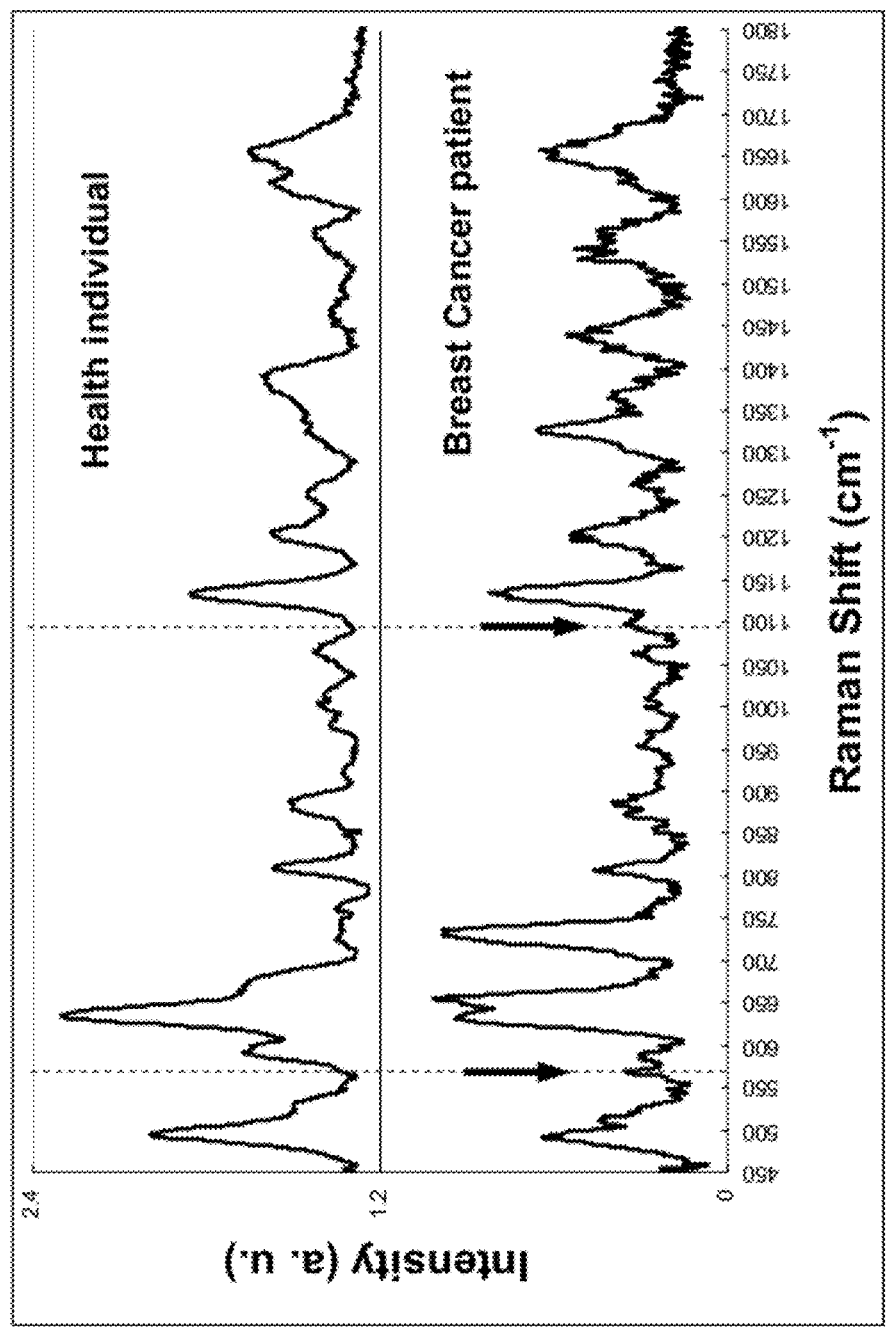
FIG. 18 illustrates an exemplified Raman spectral signature for breast cancer detected in the saliva of a breast cancer patient by the disclosed Raman scattering probe.
Figure 19A:
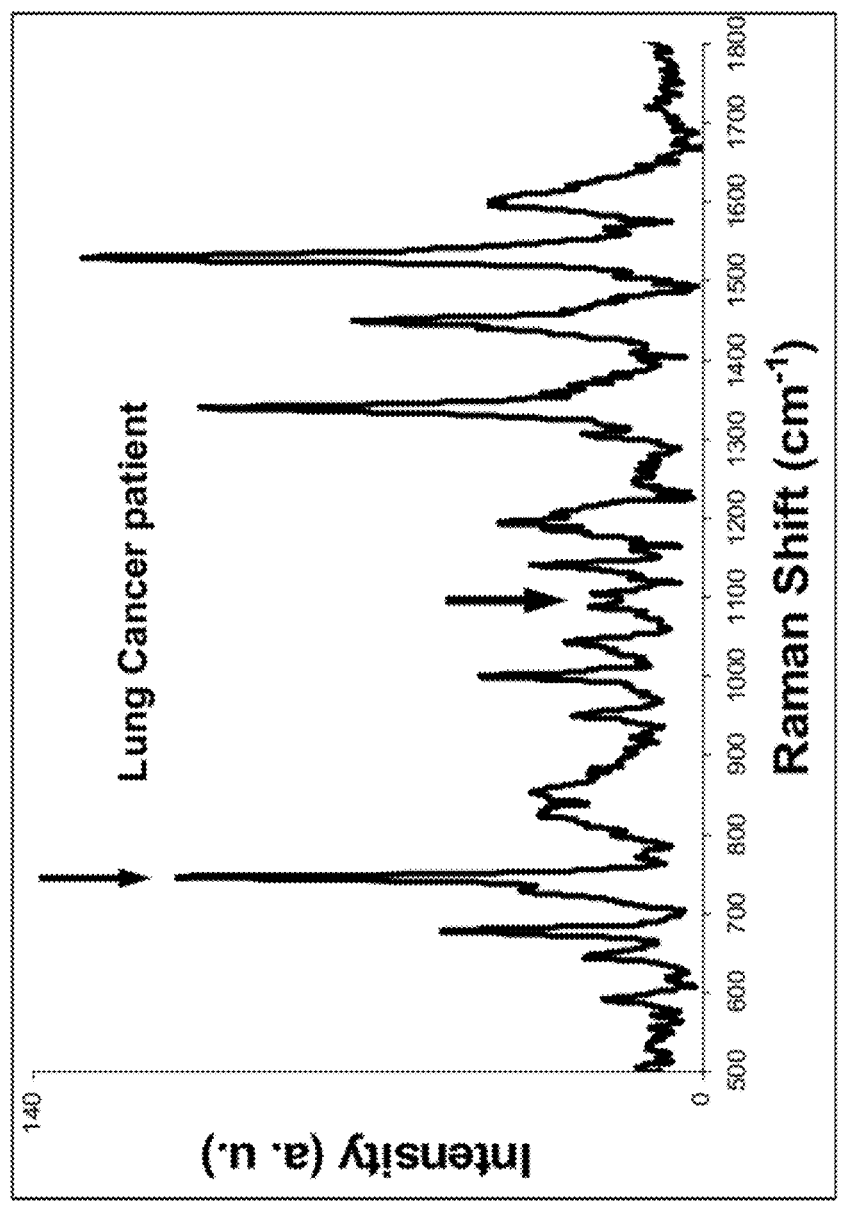
FIGS. 19A and 19B illustrate an exemplified Raman spectral signature for lung cancer detected in both the saliva and the serum of a lung cancer patient using the disclosed Raman scattering probe.
Figure 19B:
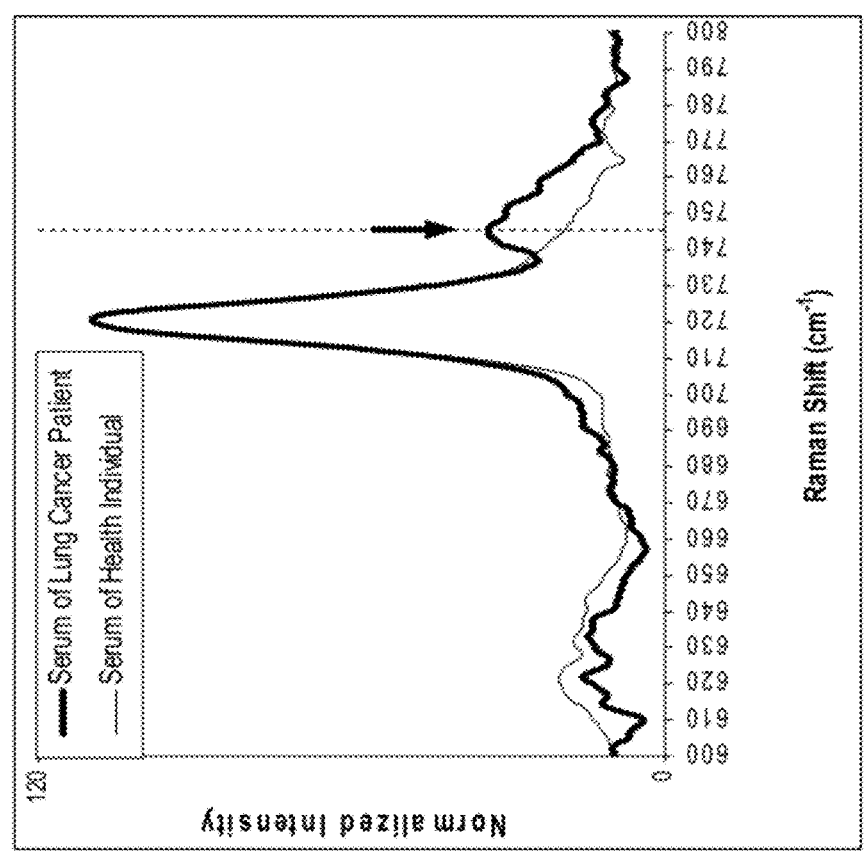
Figure 20:
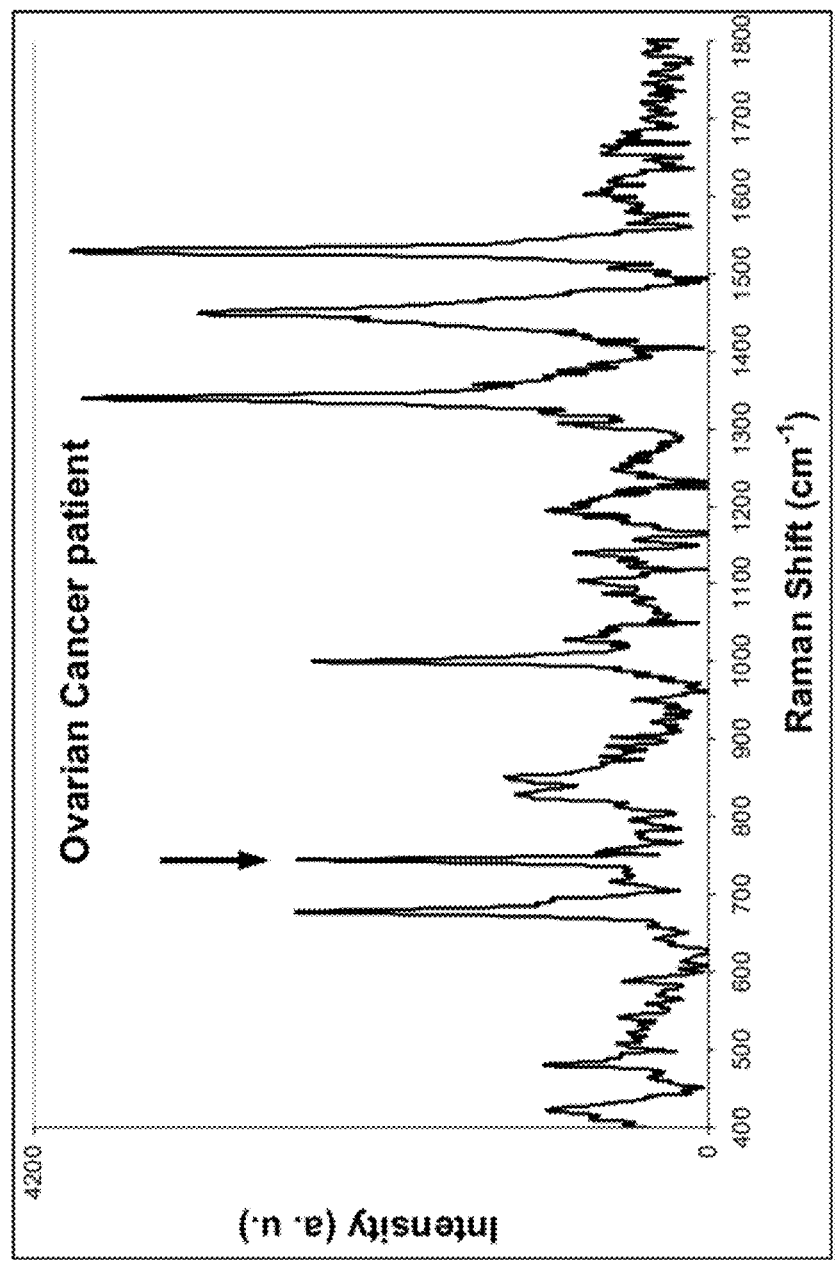
FIG. 20 illustrates an exemplified Raman spectral signature for ovarian cancer detected in the serum of an ovarian cancer patient by the disclosed Raman scattering probe.
Figure 21:
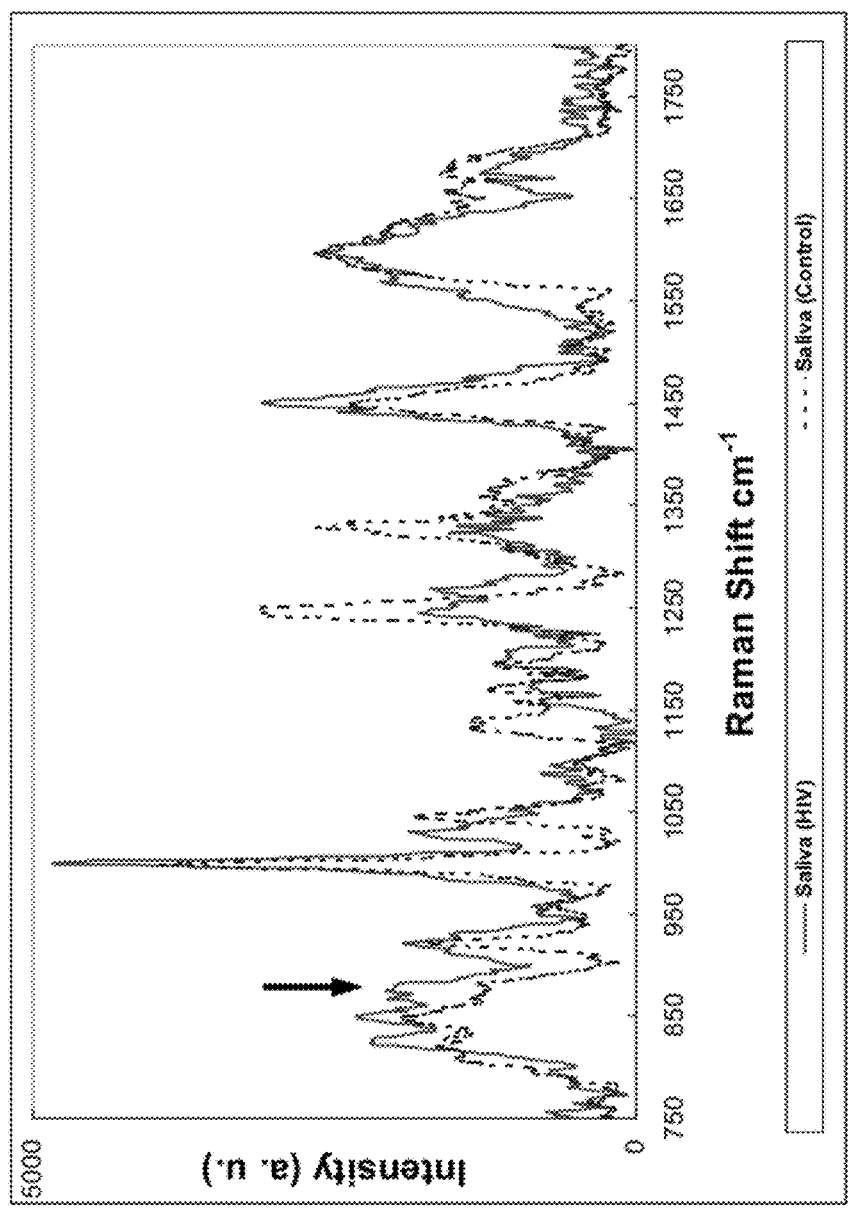
FIG. 21 illustrates an exemplified Raman spectral signature for HIV detected in the saliva of an HIV patient by the disclosed Raman scattering probe.
Figure 22:
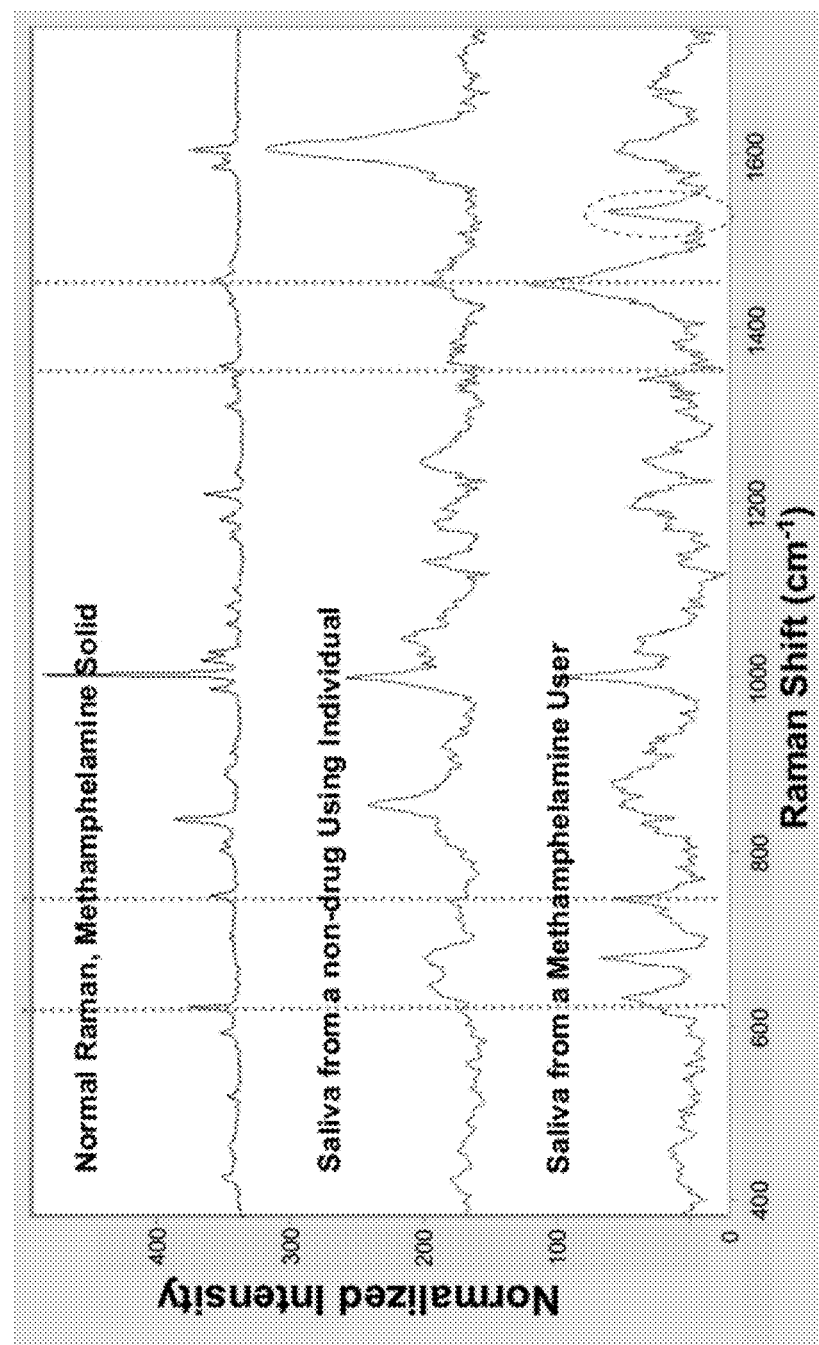
FIG. 22 illustrates an exemplified Raman spectral signature for illicit drug use detected in the saliva of an illicit drug user by the disclosed Raman scattering probe.

The disclosed systems and methods can also be used to estimate glucose level so that to evaluate diabetes status. A signature spectral peak in the region from 1115 cm$^{-1}$ to 1135 cm$^{-1}$, for example, around 1124 cm$^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 cm$^{-1}$ and 1100 cm$^{-1}$ (FIG. 18). Saliva and serum samples obtained from lung cancer and ovarian cancer patients can have a Raman spectral signature at around 745 cm$^{-1}$ (FIGS. 19 and 20). The signature spectral peak at 745 cm$^{-1}$ is associated with molecular vibrations for C—S bonds in phosphate, O—P—O vibration in Z-DNA, or T-DNA. HIV can have a spectral signature in Raman spectrum obtained from a serum sample in the region of 865 cm$^{-1}$-885 cm$^{-1}$, for example, around 870 cm$^{-1}$ (FIG. 21). The disclosed systems and methods can also be used to identify illicit drug such as heroin, methamphetamine cocaine, caffeine, morphine, codeine, amphetamine, ephedrine, papaverine, narcotine, acetyl codeine, methamphetamine HCl, ketamine HCl, codeine H$_3$PO$_4$, meperidine HCl (pethidine), triazolam, secobarbital, hypaconitine, MDMA, etc. FIG. 22 shows Raman spectra from a methamphetamine solid (a type of illicit drug), a saliva sample of a non-drug using individual, and a methamphetamine drug user. The Raman spectrum from a drug-user's saliva sample shows a characteristic peak at around 1030 cm$^{-1}$ and 1535 cm$^{-1}$, which can be used to indicate illicit drug use. The disclosed methods and systems can also be used to detect doping (e.g., hormone) in athletes during international sports competitions such as the Olympic Games.

Figure 23:
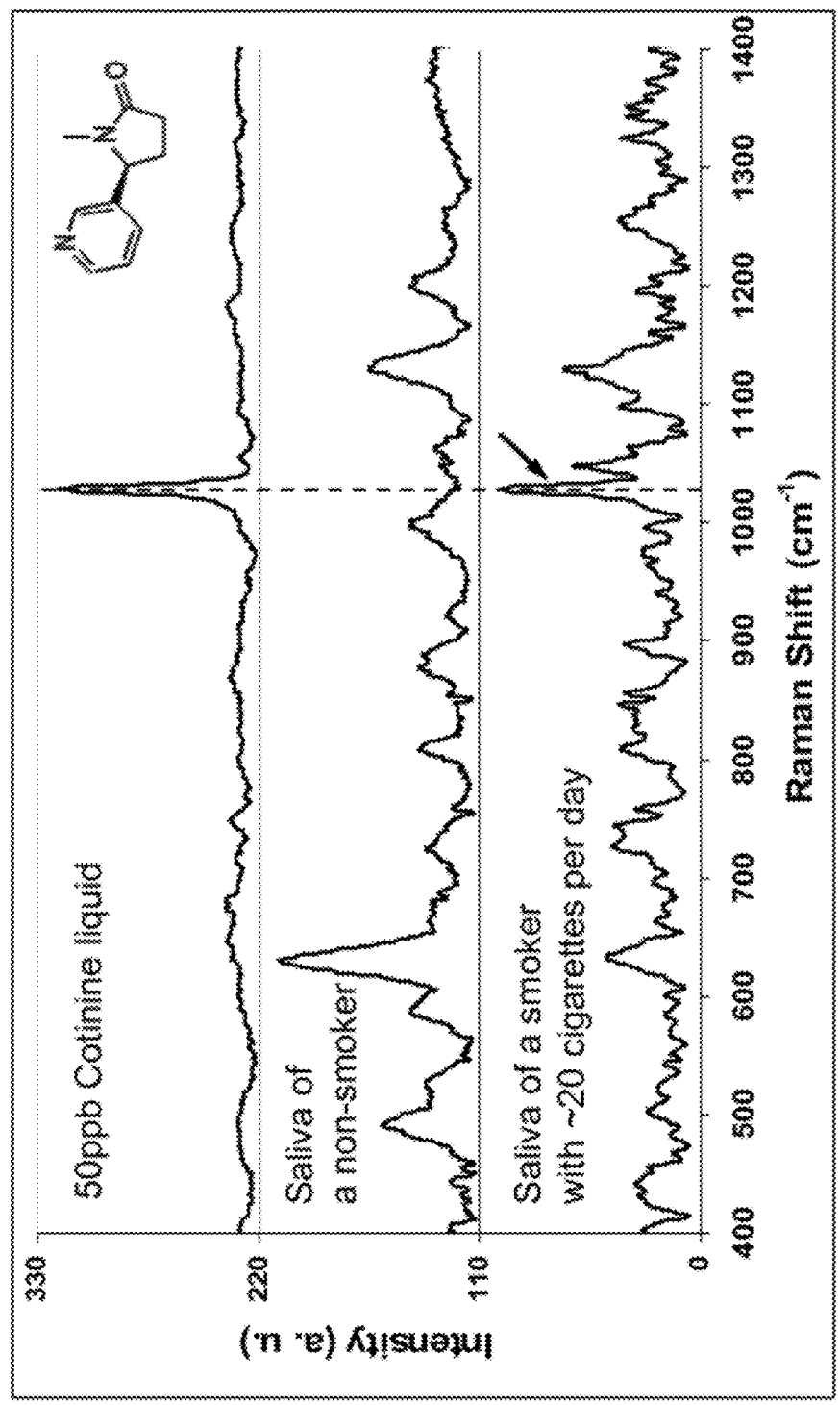
FIG. 23 illustrates an exemplified Raman spectral signature for the smoking status detected in the saliva of a smoker by the disclosed Raman scattering probe, with a comparison of a Raman spectral signature of the cotinine which is the metabolite of nicotine.

Similarly, referring to FIG. 23, smoking status or secondary smoking status can also show spectral signature at around 1029 cm$^{-1}$ in a Raman spectrum obtained from a saliva sample of a smoker, which is absent in a non-smoking healthy individual. The signature spectral peaks around 1029 cm$^{-1}$ is associated with molecular vibration mode of cotinine which is metabolite of nicotine.

Figure 24:
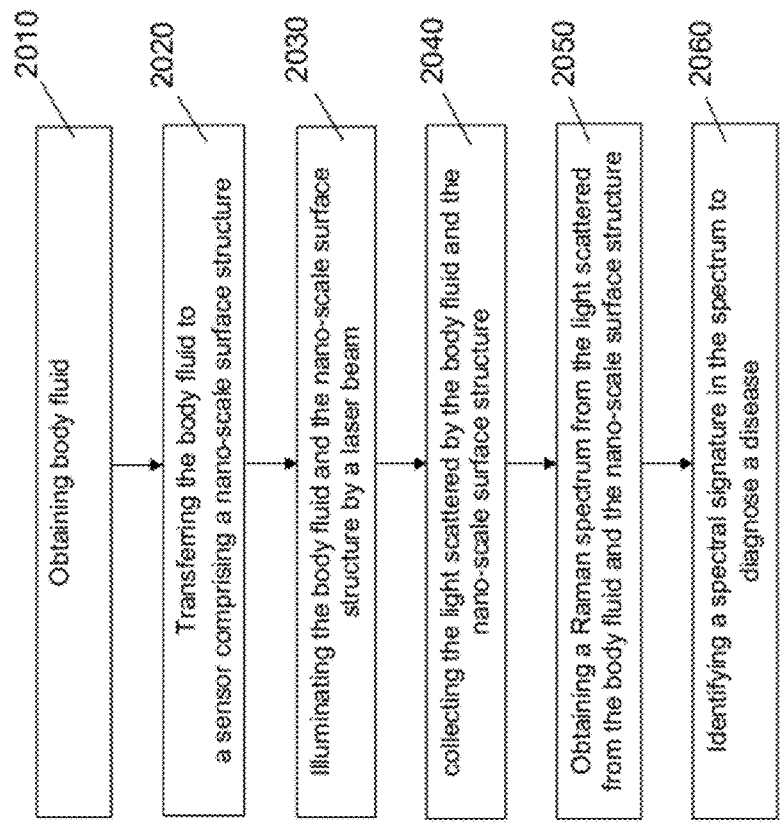
FIG. 24 is a flowchart for non-invasive disease diagnosis using the disclosed Raman scattering probe.

The non-invasive disease detection and diagnosis using the disclosed Raman scattering probe can include one of more of the following steps: referring to FIG. 24, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 4 ml. Examples of the body fluid can include blood, saliva, urine, serum, tear, sweat, stomach fluid, hydrothorax, ascites, CSF, sperm, and a secrete body fluid. After centrifuge, the body fluid is next transferred to a sensor comprising a nano-scale surface structure (step 2020). Molecules in the body fluid are adsorbed to the nano-scale surface structure. A laser beam is applied to illuminate the body fluid, the nano-scale surface structure, and the molecules adsorbed onto the nano-scale surface structure (step 2030). Light scattered by the body fluid, the nano-scale surface structure, and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include cancers including but not limited to lung cancer, breast cancer, stomach cancer, esophageal cancer, thyroid cancer, larynx cancer, ulcer cancer, ovarian cancer, liver cancer, head and neck cancers, uterus cancer, cervix cancer, oral cancer, leukemia, colon cancer, bladder cancer, prostate cancer, skin cancer, bronchus cancer, and liver cirrhosis, a failing kidney, HIV, and drug addiction. As previously described, the one or more spectral signatures are at predetermined wavelengths in the Raman spectrum. The wavelengths and the characteristics of the spectral signatures are specific to the disease to be detected. For example, spectral signatures for oral and breast cancers in a saliva sample can be at around 560 cm$^{-1}$ or 1100 cm$^{-1}$. A spectral signature for lung cancer in a serum sample can be at around 745 cm$^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

It should be noted that the steps illustrated in FIG. 24 is compatible with and can incorporate one or more steps shown in FIG. 8, which involves using a sample solution containing nano particles.

In some embodiments, the disclosed light scattering probe and disclosed chemical detection methods can be applied in food safety applications, which can include screening illegal additives and verifying useful ingredients in food products. An example for food products is dairy products. Dairy products can include milk, milk powders (e.g., baby formula), cheese, cheese-containing cakes, yogurts, ice creams, milk containing candies, milk containing cookies, milk contained food products, and protein contained food products. A recent serious issue in food safety is related to illegal melamine additive in dairy products such as baby formula, ice cream, and biscuit, etc. The disclosed methods and systems are also applicable to detecting existence and levels of methanol, in alcohol products such as wines, nitrite, sodium cyclamate (sodium cyclohexylsulfamate) and other food additives in food, beverage, alcohol products such as red wine, and wine.

As described above in relation to FIGS. 1A-2, 6A, 6C, and 7-9B, a food sample can be prepared in a solution, which is then introduced on a sensor (105 in FIG. 1A) or mixed with a sample solution (720 in FIG. 7) containing nano particles. Light scattering and Raman spectral analyses can be conducted as shown in FIGS. 1A-1C or in FIG. 7. Alternatively, the sample solution containing the nano particles can be introduced on an structured or unstructured surface of a sensor, as described above, which is used in subsequent light scattering and Raman spectral analysis.

As described above in relation to FIGS. 1A-2, 6A, 6C, and 7-9B, chemical or biological sample can be prepared in a solution, which is then introduced on a sensor (105 in FIG. 1A) or mixed with a sample solution (720 in FIG. 7) containing nano particles or carbon nano tubes. One way to prepare sample solution is to directly mix chemical and biological substance contained sample, such as liquid, solid, powder, sol gel, aerosol, etc., into test sample solution containing nano particles; the other way to prepare sample solution is to mix gas phase chemical or biological substance into the test solution using the sample tube with number of tiny holes at the end of tube emerging into a solvent solution, which gas phase sample is continuously purged into the solvent solution, then prepare the sample solution by mix the solvent solution with the solution containing nano particles. The gas purging time is in the range from 1 min to 2 hours, the gas purging pressure is in the range from 1 atm to 5 atm. the dimension of number of holes at the end the gas sampling tube is from 5 μm to 50 mm, the dimension of inner diameter of the gas sampling tube is from 20 μm to 500 mm. The chemicals containing in the gas or aerosol phase sample include ammonia, benzene, toluene, m-xylene, o-xylene, p-xylene, sulfur dioxide, nitrogen monoxide, nitrogen dioxide, neovaricaine, dimethyl formamide, etc. Light scattering and Raman spectral analyses can be conducted as shown in FIGS. 1A-1C if the sample solution is placed onto the surface of a sensor, or in FIG. 7. Alternatively, the sample solution containing the nano particles can be introduced on an structured or unstructured surface of a sensor, as described above, which is used in subsequent light scattering and Raman spectral analysis.

In some embodiments, milk sample solutions are prepared from a milk solution by respectively applying with melamine additive at concentrations of 1 ppm (parts per million), 2 ppm, 5 ppm, and 50 ppm. The milk sample solutions are separately applied to a sensor (105 in FIG. 1) or introduced into a sample solution (720 in FIG. 7) containing nano particles.

The melamine additive includes melamine and melamine cyanurate. Raman spectra are obtained using the light scattering probe and method described above. A typical volume for the food sample solution is in a range from about 100 pl to 1 ml.

Figure 25A:
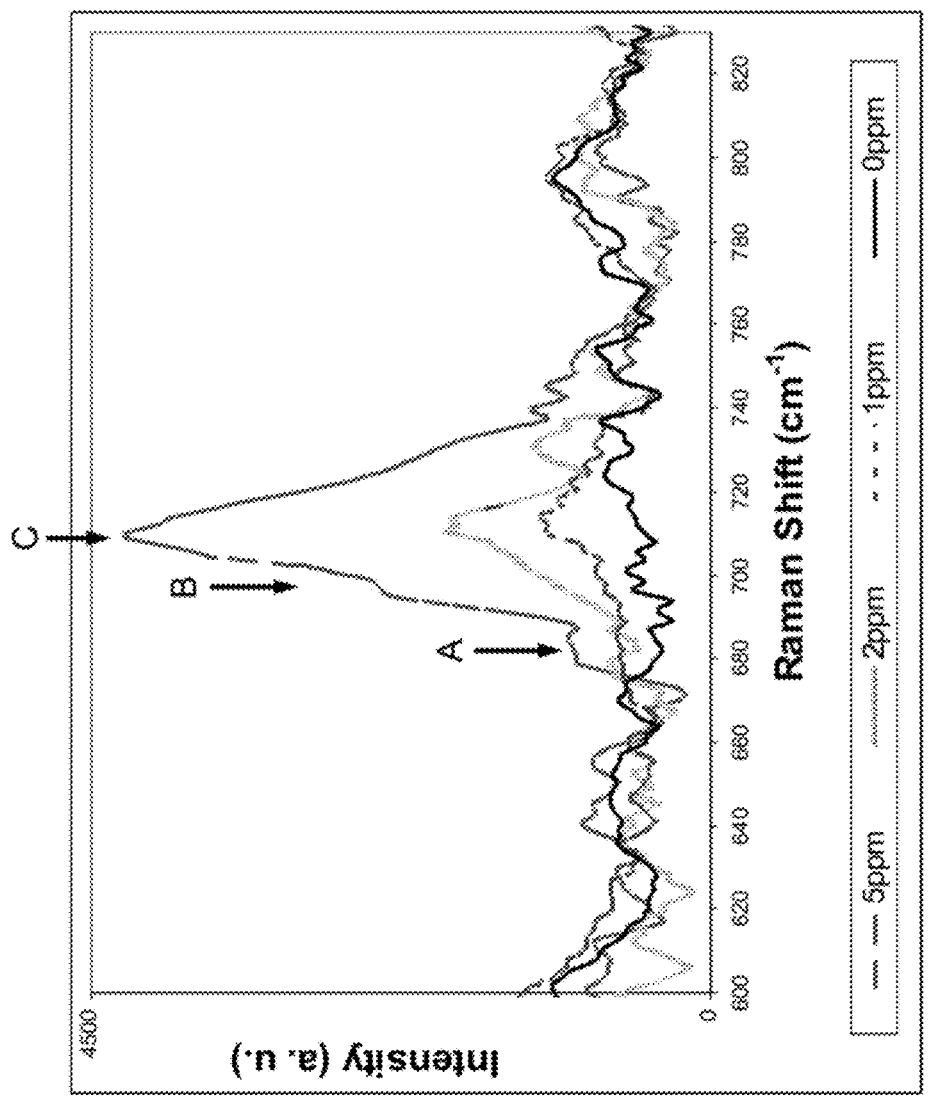
FIGS. 25A and 25B illustrate Raman spectra having spectral signatures for an illegal and harmful chemical (melamine) detected at different concentration levels in a milk product.
Figure 25B:
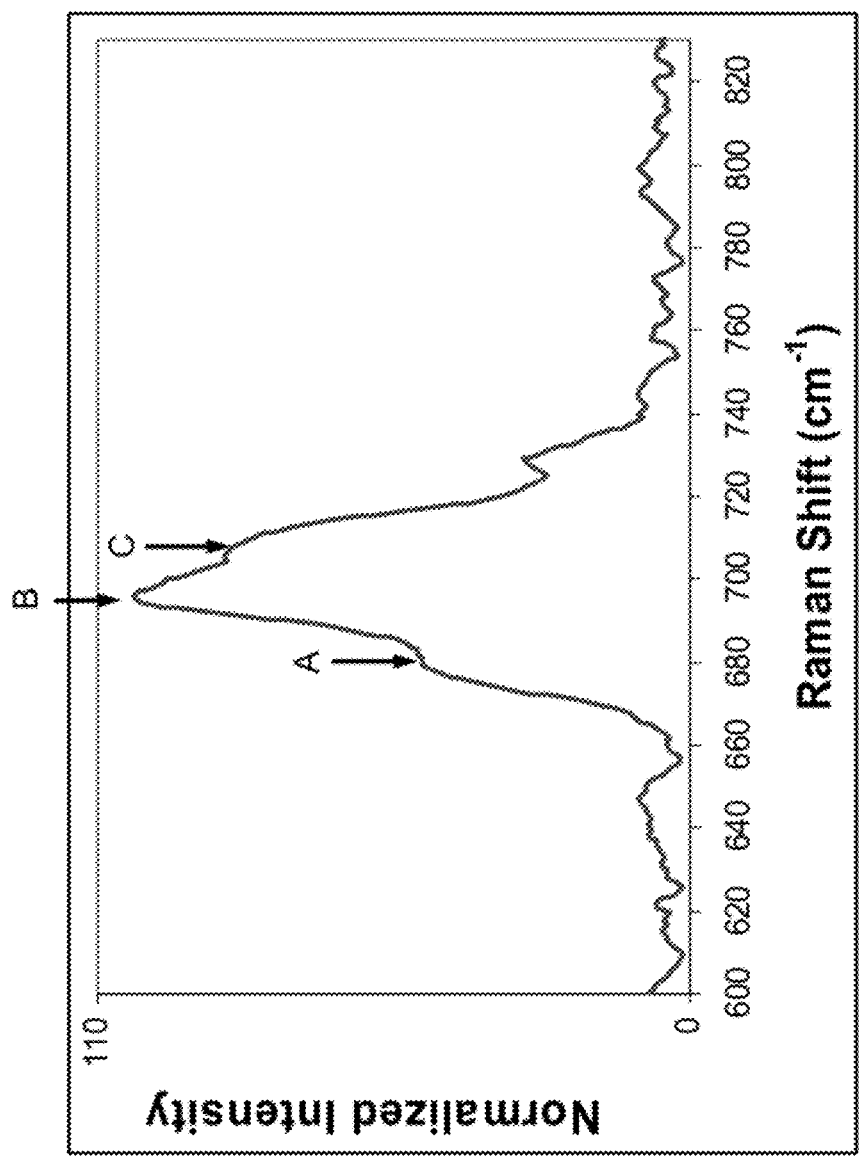

Raman spectra having spectral signatures for an illegal and harmful chemical (melamine) detected at different concentration levels in a milk product. FIG. 25A illustrates Raman spectra obtained from the milk sample solutions with melamine additive respectively at 0 ppm (no melamine additive), 1 ppm, 2 ppm, and 5 ppm concentration levels. FIG. 25B illustrates a Raman spectrum obtained from the milk sample solution having melamine additive at 50 ppm level. The Raman spectra shown in FIGS. 25A and 25B comprise Raman signature bands around 700 $cm^{-1}$, which are approximately at around 678 $cm^{-1}$ (Band A), 698 $cm^{-1}$ (Band B), and 712 $cm^{-1}$ (Band C), respectively. These observed Raman peaks are assigned to be vibration of the ring breathing II mode and involves in-plane deformation of the triazine ring of melamine molecule, or a ring out of-plane bending vibration of melamine cyanurate molecule. Moreover, it was observed that Band A at around 678 $cm^{-1}$ increases in relative strength among the three bands as the melamine concentration is increased. In contrast, Band C at about 712 $cm^{-1}$ decreases in relative strength as melamine concentration increases. These two trends can be clearly seen by comparing the Raman spectra at the 5 ppm (FIG. 25A) and 50 ppm (FIG. 25B) melamine levels. Note that melamine cyanurate (needle-shaped micro-sized white precipitates) is formed when melamine and cyan uric acid exist in the solution together under certain condition.

Figure 26:
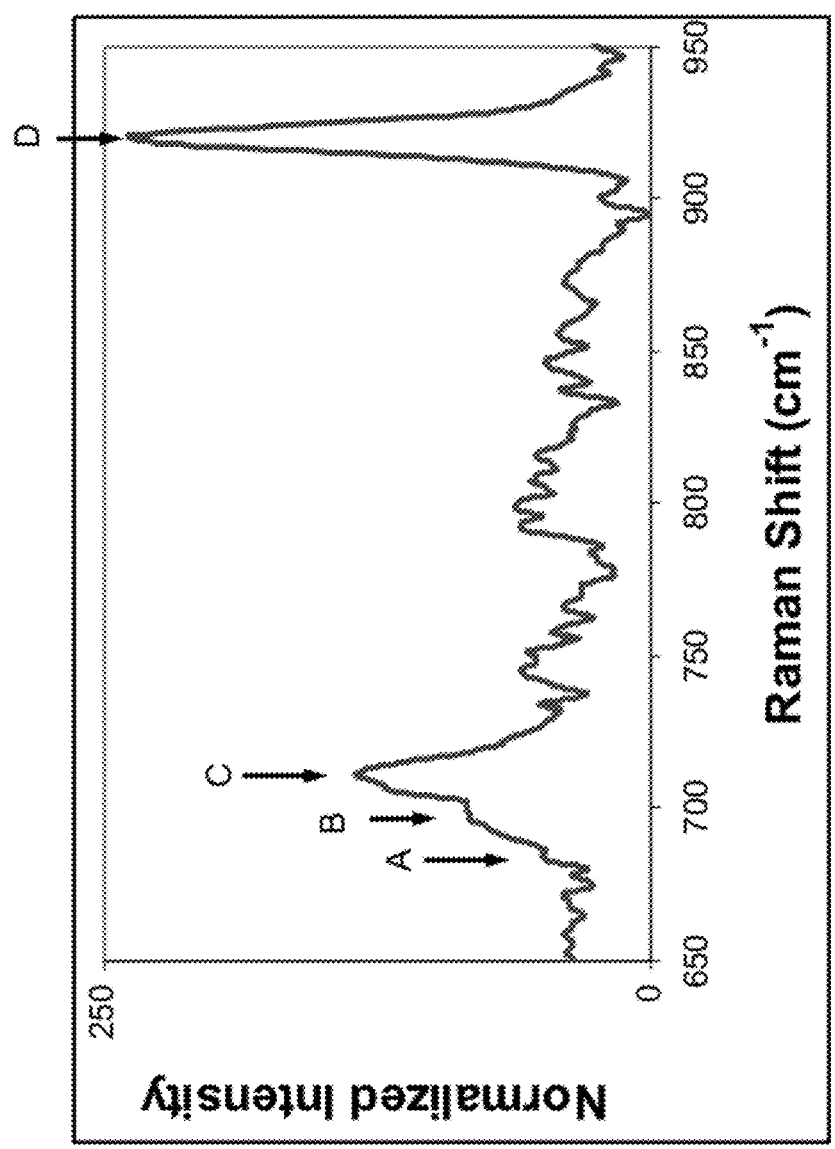
FIG. 26 illustrates a Raman spectrum having a spectral signature for melamine detected in a milk solution using around 918 cm$^{-1}$ Raman band of the acetonitrile as an internal standard reference.

In another example, acetonitrile solvent can be added to a sample milk solution as an internal standard reference for the Raman scattering measurement. Acetonitrile is used as a solvent because it was found that the Raman scattering strength is not or weakly coupled to test solution. Referring to FIG. 26, a Raman spectrum is obtained, with the Raman spectral signature around 700 $cm^{-1}$ (Band A, B and C), from a milk solution having a melamine concentration at 5 ppm and with the addition of the acetonitrile using the above described system and methods. A Raman band (Band "D") is found at around 918 $cm^{-1}$-921 $cm^{-1}$, which can be used as an internal standard reference for calibrating Raman band frequency and intensity. Another Raman band exists at around 1640 $cm^{-1}$.

Figure 27:
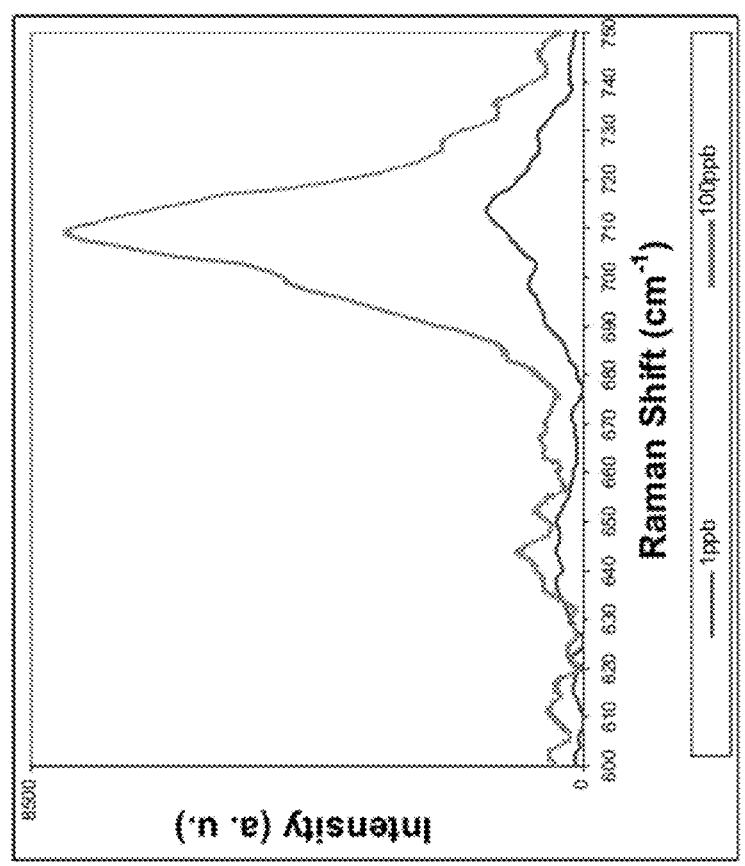
FIG. 27 illustrates Raman spectra having spectral signatures for an illegal and harmful chemical (melamine) detected at different concentration levels in water.

In another example, Raman spectra having spectral signatures for an illegal and harmful chemical (melamine) detected at different concentration levels, 1 ppb (parts per billion) and 100 ppb, in aqueous solution (FIG. 27).

In some embodiments, referring to FIG. 1B, FIGS. 16F, 16E, and 16H, a metal film is coated on the nano rods 108 (or holes) on the nano surfaces of the sensor 105. The metallic film is electrically connected to an electrode. The metallic film can be formed by a noble metal such as gold. To apply a sample solution to the sensor surface, the sensor is submerged in the sample solution. An electric bias potential is applied to the electrode and the metallic film. The electrical bias potential can be controlled in the range from −3.0 to +3.0V, which can enhance the adsorption of the sample molecules (e.g., melamine molecules) to the nano surfaces, to enhance local electro-magnetic filed, and enhance charge transfer between sample molecules and nano surface structures, which can enhance the intensity of Raman scattering from the sample molecules adsorbed on the nano surfaces. The incident laser beam can be projected on the sensor and the scattered light detected while the potential bias is being applied to the sample solution. The Raman light scattering measurement can also be conducted after the electrical bias potential is withdrawn.

In some embodiments, ion-exchange column is a means of separation of interferences from the samples. After sample passed the column, interferences retain on the column and analytes are flute out. The column, for example, $C_{18}$ column, also can be employed that can separate chemicals in different retention times that chemical properties are similar. The final purified sample would result in increasing the limit of detection up to 2-6 orders.

In some embodiments, the detection of chemicals in food or for disease diagnosis can be conducted using an integrated device that is capable of chemical separation and light scattering detection of trace chemicals, biological materials, etc. Details about such an integrated device are disclosed in commonly assigned U.S. patent application Ser. No. 11/761,453, entitled "Integrated Chemical Separation Light Scattering Device", filed on Jun. 12, 2007, the disclosure is incorporated by reference herein.

Figure 28:
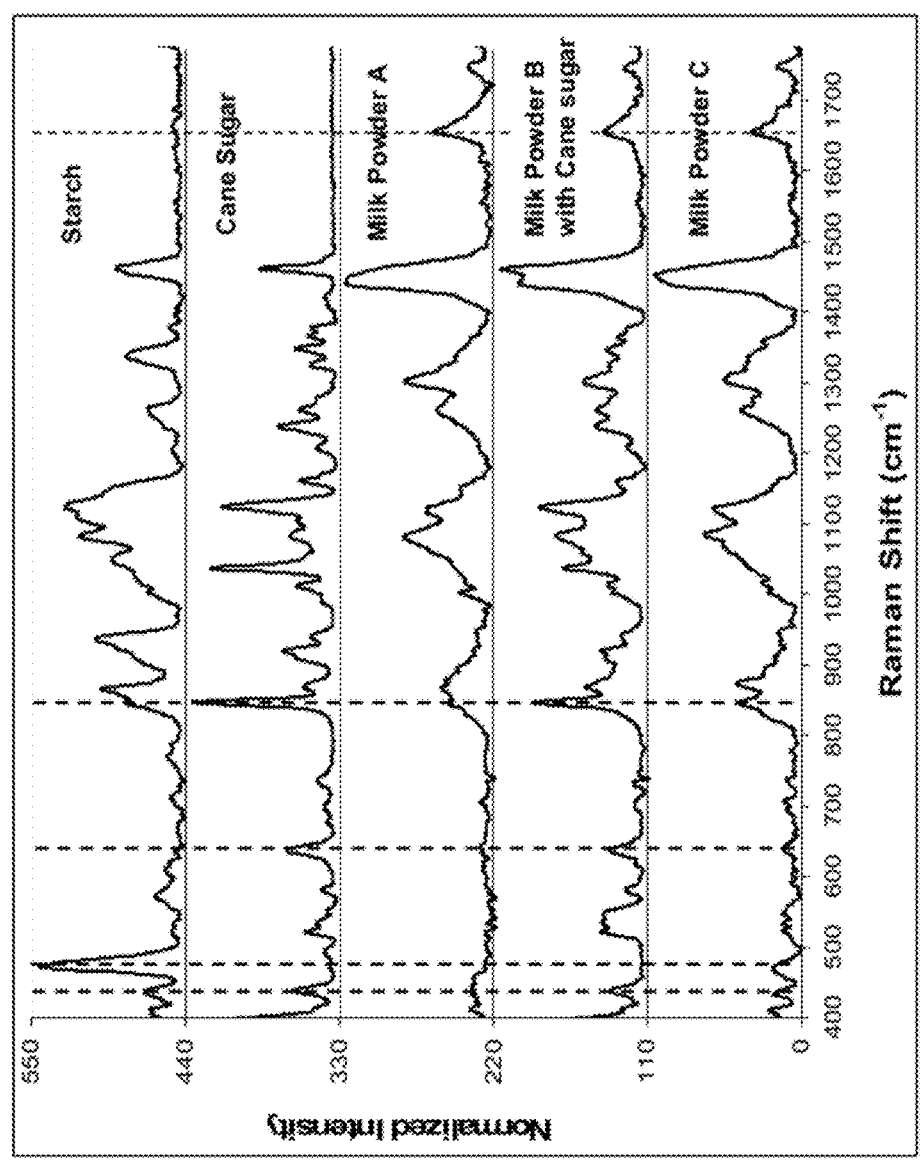
FIG. 28 illustrates Raman spectra for identifying unauthorized additive chemicals in a milk powder product.

In some embodiments, the disclosed light scattering probe and disclosed chemical detection methods can also be applied to detect useful or neutral ingredients as well as illegal or harmful ingredients in food products. FIG. 28 illustrates, from top to bottom, Raman spectra from starch, cane sugar, a milk powder A (a first milk powder brand), a milk powder B (a second milk powder brand) containing with cane sugar additive, and milk powder C (a third milk powder brand). Starch and cane sugars are not supposed to be in normal milk powders. But because starch and cane sugars are white powders, they are not easily detected with normal test methods when they are mixed in milk powder. The Raman spectrum (at the top of FIG. 28) shows a very strong band at around 473 $cm^{-1}$, which provides an evidence for starch content in a milk powder. This signature Raman band can be used to detect if starch is mixed into milk power. The detection method is applicable to the unauthorized mixing of starch containing materials such as flour, rice powder, soybean powder, potato powder, sweet potato powder, etc.

The disclosed systems and methods can also be used to screen the existence of cane sugar in milk powders. The Raman spectra (second from the top in FIG. 28) shows several strong Raman bands (around 850 $cm^{-1}$, 940 $cm^{-1}$, 1020 $cm^{-1}$, 1130 $cm^{-1}$ and so on). The collective characteristics of these Raman bands are visible in the spectrum obtained from milk powder B mixed with cane sugar (fourth from the top in FIG. 28), which is legal since the milk powder B package labeled related cane sugar mixing, but absent from the spectrum obtained from milk powder A without cane sugar additive (third from the top in FIG. 28). On the other hand, the collective characteristics of cane sugar related Raman bands are visible in the spectrum obtained from milk powder C (bottom spectrum of FIG. 28), which the milk powder is illegal sine its package label didn't show related cane sugar. Note that Raman test shows that milk powder C was mixed with both starch and cane sugar without package labeling.

Furthermore, the disclosed methods and systems can be applied to determine level of protein contained in a food product such as in a dairy product. A high concentration of protein in a food product can be reflected by high amide I concentration which carries Raman signature band at around 1658 $cm^{-1}$. The intensity at 1658 $cm^{-1}$ relative to other spectral features can be used to quantify the protein level in a food product such as a milk powder. For example, the three different samples of milk powders in FIG. 28 (shown in the lower three spectra in FIG. 28) are of similar protein levels. The more pronounced peak at 1658 $cm^{-1}$ for milk powder A shows milk powder A contains slightly higher protein level than milk powder B and milk powder C.

The disclosed methods and systems are therefore effective means for detecting protein levels, the existence of cane sugar, starch, and illegal additives such as melamine in milk powders. Moreover, the disclosed systems are compact and portable. The substance detection can be easily conducted on site with a fast turn around time (5 to 10 minutes or even shorter time), which can enable timely and effective authentication and quality verification of milk contained products, such as milk and powder in a wide range of circumstances.

Intensity of Raman signals can be increased by pre-treatment of the test sample. For example, after the test sample is dissolved in a solution, solid particles, unwanted ionic molecules, or undisclosed materials can be removed from the solution by filtering solution using a solid-phase extraction (SPE) column which the major steps include pre-condition by certain solvents, passing sample solution through the column, washing the column by some selected solutions, and obtaining final elute analyte for determination, which is then subject to the light scattering analysis. The removal of solid particles, unwanted molecules, or undisclosed materials can significantly reduced noises in the scattered light from the nano structured surface of a chemical sensor or from a sample solution containing nano particles, so that one is able to carry out quantitative analysis of targeted molecule concentration in know base materials, for example, down to 0.5 ppm concentration of melamine in fresh milk or in product milk, or in milk powder.

When the disclosed methods and systems are applied to food inspection, illegal food additive molecules can be separated from food matrix materials by controlling (e.g. raising) temperature of the sample solution (e.g. 720 in FIG. 7). An illegal food additive is Sudan I which can be separated from capsorubin by controlling temperature in a range of 20° C.-100° C., more specifically from 40° C. to 80° C., for the period from 1 sec-30 min, or a period from 1 min to 10 min. Other illegal food additives detectable by the disclosed methods and systems include Rhodanmine B, Benzoic acid (sometimes found in milk products), hyposulfurous acid, sodium formaldehyde, crysoidine G, boric acid and borax, sodium sulfocyanate, rhodanmime B, Lead chrome green, Basic Flavine O, industrial used formaldehyde and NaOH, carbon monoxide, sodium sulfate, industrial surfer, industrial dyes, fructus papaveris, over dosed level of food colorants (e.g. carmine, lemon yellow, allura red AC, sunset yellow, etc.), food preservants, sweeteners (e.g., saccharin sodium salt, Sodium cyclamate), emulsifier (sucrose easter of fatty acid, etc.), swelling agents overdose ($KAlSO_4$, $NH_4AlSO_4$, etc.), bleach, sulfer suffumigation, color protectants (nitrate, nitrite, etc.), $TiO_2$, benzoyl peroxide, and $KAlSO_4$. In some embodiments, proteins are separated from mil sample before the detection of melamine using Raman scattering. Proteins can be precipitated or chemically separated from fresh milk or milk powder solution. In one example, the milk solution can be mixed with a high concentration (e.g. super-saturated concentration) of salt such as NaCl to precipitate proteins. In another example, an acetone in acid condition can be added to the milk solution to precipitate proteins. SPE column also be used to remove proteins in the milk solution. The resulting colorless transparent solution is then subject to Raman scattering testing as described above. The removal or precipitation of proteins can significantly reduce random scattering in the Raman spectral signals and thus can significantly increase sign-to-noise ratio in the disclosed techniques, which allows detection melamine at a concentration of 0.2 ppm in fresh milk.

Figure 29:
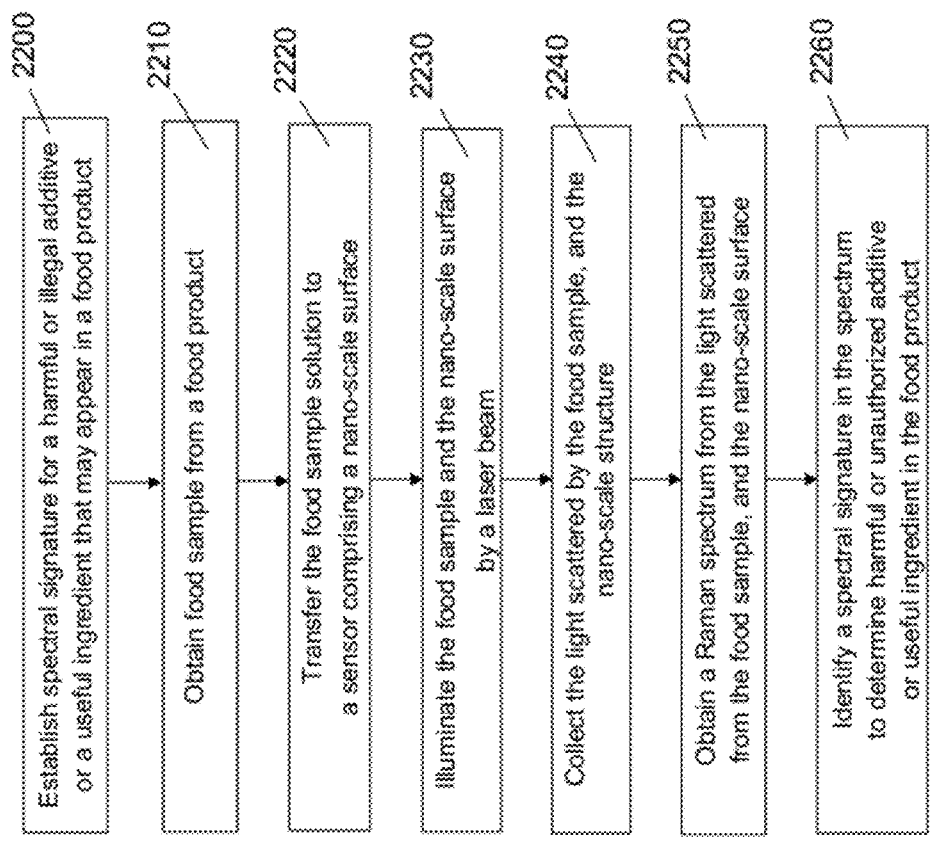
FIG. 29 is a flowchart for detecting harmful chemicals in food products for assuring food safety.

The detection of harmful chemicals in food products using the disclosed Raman scattering probe can include one of more of the following steps: referring to FIG. 29, spectral signatures for harmful or unauthorized, useful ingredients or protein (amide I) that may appear in a food product are first established (step 2200). This can be achieved by conducting Raman scattering measurement on a reference solution of a harmful or useful ingredient applied to nano surface structures on a light scattering sensor as described above. The wavelengths and spectral characteristics (peak height, peak width etc.) can be stored in a library in the spectral analyzer (150 in FIG. 6A). A threshold value can also be determined for the peak height of the spectral signature, which can correspond to certain predetermined concentration of the chemical in the reference solution. In some embodiments, the signal-to-noise ratio of the spectral peak is calculated. The chemical can be positively identified, if the signal-to-noise ratio is above certain threshold (such as 3).

In some embodiments, the sensor used for establishing the spectral signature includes substantially the same nano structures as the sensors to be used for detecting or quantifying chemical substance in the food products. In other words, the dimensions and shape of the nano rods or nano holes, the spacing between the nano rods and nano holes, as well as the material compositions of the nano rods and nano holes are substantially the same for the sensor used for establishing the spectral signature and for in-field testing of food product. For instance, the same sensor model can be used for both purposes. This approach can assure the best matching of spectral characteristics between a measured spectrum and a spectral signature. The approach can also minimize noise that can be caused by structural differences between different sensor structures and material compositions.

In some embodiments, the nano surface structure used for establishing Raman spectral signature for a chemical can be prepared by a test solution that includes the target chemical and a suspension of nano particles. The original sensor surface can be relatively flat. The test solution is applied to the sensor surface. After evaporation, a layer of nano particles adsorbed with the target chemical's molecules are deposited on the sensor surface, which is subject to Raman scattering measurement for establishing the Raman signature. The same procedure can be followed in detection of an ingredient in a food product or a substance in a body fluid from a patient except that the target chemical is replaced by a sample solution of the food sample or the body fluid. To improve test sensitivity and reduce noise in the analysis, the same nano particles and the same solvent are preferably used for the Raman signature testing and the in-field substance detection. In other words, the size distribution and material composition of the nano particles used in establishing the Raman spectral signature and the in-field measurement can be substantially the same.

A food sample is first obtained from a food product (step 2210 in FIG. 29). Due to the high sensitivity of the disclosed Raman scattering sensors, the amount food sample solution can be rather small. For example, the volume of the food sample solution obtained from the field can be in a range from about 100 pl to 1 ml. Examples of the food sample can include dairy products, candies, drinks, alcohol, meat, water products (such as fish, shrimp, etc.), tea, fresh or canned vegetables, fruits, grain products, cereals, corn chips, or potato chips, etc. The food sample can be prepared or dissolved in a solution and transferred to a sensor comprising a nano-scale surface structure (step 2220). Molecules in the food sample solution are adsorbed to the nano-scale surface structure. A laser beam is applied to illuminate the food sample solution, the nano-scale surface structure, and the molecules adsorbed onto the nano-scale surface structure (step 2230). Light scattered by the food sample solution, the nano-scale surface structure, and the adsorbed molecules is collected (step 2240). The test can also be carried out with mixing test sample with test reagent containing noble metal (such as silver Ag, gold Au, etc.) nano particles with averaged particle diameter in the range of about 2 and about 100 nm, Then, light scattered by the mixed sample solution, with or without the nano-scale surface structure, and the adsorbed molecules is collected (step 2240).

A Raman spectrum is obtained from the scattered light (step 2250). One or more spectral signatures are identified in the spectrum to determine harmful or illegal additives and ingredients, or to verify the existence and concentration levels of useful ingredients (step 2260). Examples of the harmful or illegal additives or ingredients, common fertilizer chemicals, weed control chemicals, pesticides, insecticides, antibiotics, hormones, heavy metals, toxic materials, hazardous chemicals, and preserving chemicals, including but not limited to melamine, sodium cyclamate (sodium cyclohexylsulfamate) cane sugar, starch, nitrite, nitrate, sulfide (e.g., NaS), Sudan I, II, III and IV, malachite green, formaldehyde, methomidophos, acephate, DDT, DDV, malathion, fenitrothion, malathion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methy parathion, phosmet, nitrofuran (for example, furanzolidole), dimethoate, chloramphenicol, chlortetracycline, ciprofloxacin, clenbuterol, enorfloxacin, phthalates, dioxins, heavy metals in water including but not limited to Pd, Cd Hg, As, Cr, cyanides (e.g., KCN, NaCN), chlorates, sulfates, etc. Wavelengths and the characteristics of the relevant spectral signatures in Raman spectra are specific to each chemical to be detected or quantified, as described above in relation to FIGS. 25A-28. A spectral signature can include a spectral peak. The spectral signature can be identified when the spectral peak is above certain threshold, which can be predetermined by analyzing the reference solutions containing the chemical as described above. For example, a signal-to-noise ratio of the spectral peak relative to the noise background can be above 3 for the spectral signature to be positively identified.

It should be noted that the steps illustrated in FIG. 29 is compatible with and can incorporate one or more steps shown in FIG. 8, which involves using a sample solution containing nano particles.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention. For example, nano surface structures applicable to the disclosed systems and methods are not limited to the examples described. The nano surface structures can include nano rods (or columns), nano holes (or pores), and other nano surface textures, and a deposit of nano particles coated on a sensor surface. The communications between the probe assemblies and the control center can be conducted using a combination of wireless and wired communication methods. The wireless communication can be conducted using protocols and standards other than the ones described above. The spectral data can be analyzed by spectral methods other than Raman spectrum. The nano structures on the sensor surface are not limited to the examples described above to enhance the scattering spectral signals. Furthermore, the probe assemblies do not have to be installed on vehicles and flying objects instead of stationary objects.

What is claimed is:

1. A sensor-network system for spectrally sensing a chemical or biological substance, comprising:
   a plurality of probe assemblies each comprising:
      a sensor comprising a nano structured surface configured to adsorb molecules of a sample material captured adjacent to the sensor;
      a laser configured to emit a laser beam to illuminate the molecules adsorbed to the nano structured surface; and
      a spectrometer configured to obtain spectral data from light scattered by the molecules adsorbed to the nano structured surface; and
   a control center, comprising:
      a computer storage configured to store one or more spectral signatures each associated with a chemical or biological substance; and
      a spectral analyzer in communication with the computer storage, wherein the spectral analyzer is configured to determine, in the spectral data, a spectral signature matching at least one of the spectral signatures stored in the computer storage thereby to identify, in the sample material, the chemical or biological substance associated with the one of the spectral signatures.

2. The sensor-network system of claim 1, wherein at least one of the plurality of probe assemblies further comprises collection optics configured to collect the light scattered by molecules adsorbed to the nano structured surface and direct the scattered light to the spectrometer.

3. The sensor-network system of claim 1, wherein the spectral data is transmitted from the probe assemblies to the control center via a wired computer network.

4. The sensor-network system of claim 1, wherein the control center further comprises an alert and response system in communication with the spectral analyzer, wherein the alert and response system is configured to send out an alert signal when the identified chemical or biological substance is a hazardous material.

5. The sensor-network system of claim 1, further comprising a first antenna in communication with the one of the probe assemblies, wherein the first antenna is configured to transmit a first wireless signal comprising the spectral data, wherein the control center comprises:
  a second antenna configured to receive the first wireless signal; and
  a wireless router in communication with the spectral analyzer, wherein the wireless router is configured to extract the spectral data from the first wireless signal.

6. The sensor-network system of claim 5, wherein the control center further comprises an alert and response system in communication with the spectral analyzer and the wireless router, wherein the alert and response system is configured send out an alert signal when the identified chemical or biological substance is a hazardous material, wherein the wireless router is configured to transmit a second wireless signal comprising the alert signal.

7. The sensor-network system of claim 1, wherein the nano structured surface on the sensor comprises nano particles supplied by a solution.

8. The sensor-network system of claim 7, wherein the substrate comprises a substantially flat surface on which the nano particles are disposed.

9. The sensor-network system of claim 1, wherein the plurality of probe assemblies are installed in or around a building, an airport, a custom, a conveyance system for cargo or luggage, a doctor or a health advisor's office, a check station on a road, a harbor, in a vehicle, a ship, a submarine, an airplane, a train, a subway, an industrial site, a resort area, a shopping mall, a research Lab, a school, or a water source.

10. The sensor-network system of claim 1, wherein the spectral data comprises information about a Raman spectrum.

11. The sensor-network system of claim 1, wherein the sample material is extracted from a food product.

12. The sensor-network system of claim 1, wherein the sample material comprises a body fluid obtained from a person or an animal, the method further comprising: diagnosing a disease in a person or an animal based on the spectral signature determined in the Raman spectrum.

13. The sensor-network system of claim 1, wherein the plurality of probe assemblies are disposed for security monitoring, wherein the sample material to be captured adjacent to the sensor comprises a material for a chemical or a biological weapon, an explosive material, a flammable material, a narcotic drugs, or a radioactive material.

14. A sensor-network system for spectrally sensing a chemical or biological substance, comprising:
  a plurality of probe assemblies at a plurality of locations, each probe assembly comprising:
    a sensor configured to receive molecules of a sample material captured adjacent to the sensor;
    a laser configured to emit a laser beam to illuminate the molecules; and
    a spectrometer configured to obtain spectral data from light scattered by the molecules in the sensor; and
  a control center, comprising:
    a computer storage configured to store one or more spectral signatures each associated with a chemical or biological substance;
    a spectral analyzer in communication with the computer storage, wherein the spectral analyzer is configured to determine, in the spectral data, a spectral signature matching at least one of the spectral signatures stored in the computer storage thereby to identify, in the sample material, the chemical or biological substance associated with the one of the spectral signatures; and
    a processor configured to calculate a location of the sample material at a specific a time using the spectral data obtained from two or more of the plurality of probe assemblies and using the locations of the two or more of the plurality of probe assemblies.

15. The sensor-network system of claim 14, further comprising a camera adjacent to at least one of the probe assemblies, wherein the camera is configured to capture images to be evaluated by the processor to enable the identification of a suspect person or package for carrying a source of the sample material.

16. The sensor-network system of claim 14, wherein the processor is configured to determine a spatial-time profile for the source of the sample material using the spectral data obtained from two or more of the plurality of probe assemblies and using the locations of the two or more of the plurality of probe assemblies.

17. The sensor-network system of claim 14, wherein the spectral data is transmitted from at least one of the probe assemblies to the control center via a wired data line or a wired computer network.

18. The sensor-network system of claim 14, wherein the control center further comprises an alert and response system in communication with the processor, wherein the alert and response system is configured to send out an alert signal when the chemical or biological substance is identified to be a hazardous material.

19. The sensor-network system of claim 14, further comprising a first antenna in communication with the one of the probe assemblies, wherein the first antenna is configured to transmit a first wireless signal comprising the spectral data, wherein the control center comprises:
  a second antenna configured to receive the first wireless signal; and
  a wireless router in communication with the spectral analyzer, wherein the wireless router is configured to extract the spectral data from the first wireless signal, wherein the wireless router is configured to transmit a second wireless signal comprising an alert signal when the identified chemical or biological substance is a hazardous material.

20. The sensor-network system of claim 14, wherein the sensor comprises a nano structured surface configured to adsorb molecules of the sample material captured adjacent to the sensor.

21. The sensor-network system of claim 14, wherein the plurality of probe assemblies are installed in or around a building, an airport, a custom, a conveyance system for cargo or luggage, a doctor or a health advisor's office, a check station on a road, a harbor, in a vehicle, a ship, a submarine, an airplane, a train, a subway, an industrial site, a resort area, a shopping mall, a research Lab, a school, or a water source.

22. The sensor-network system of claim 14, wherein the spectral data comprises a Raman spectrum.

23. A sensor-network system for spectrally sensing a chemical or biological substance, comprising:
  a plurality of probe assemblies each comprising:
    a sensor comprising a nano structured surface that is configured to adsorb molecules of a sample material captured adjacent to the sensor; and
    a laser configured to emit a laser beam to illuminate the molecules adsorbed to the nano structured surface, wherein the probe assembly is configured to transmit the light scattered by the molecules adsorbed to the nano structured surface to a control center in an optical fiber; and a control center, comprising:
an optical multiplexer configured to receive the light scattered by the molecules adsorbed to the nano structured surface from the plurality of probe assemblies in a plurality of channels and output scattered light in one of the plurality of channels;
a spectrometer configured to obtain spectral data from the scattered light in one of the plurality of channels output by the optical multiplexer;
a computer storage configured to store one or more spectral signatures each associated with a chemical or biological substance; and
a spectral analyzer in communication with the computer storage, wherein the spectral analyzer is configured to determine, in the spectral data, a spectral signature matching at least one of the spectral signatures stored in the computer storage thereby to identify, in the sample material, the chemical or biological substance associated with the one of the spectral signatures.

24. The sensor-network system of claim 23, wherein the sample material is extracted from a food product.

25. The method of claim 1, wherein the chemical or biological substance is selected from the group consisting of melamine, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, enorfloxacin, rhodanmine B, benzoic acid, hyposulfurous acid, sodium formaldehyde, formaldehyde, phthalates, dioxins, Pd, Cd Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants, food preservants, sweeteners, emulsifier, swelling agents overdose, bleach, sulfer suffumigation, color protectants, $TiO_2$, benzoyl peroxide, and $KAlSO_4$.

26. The sensor-network system of claim 23, wherein the sample material comprises a body fluid obtained from a person or an animal, the method further comprising: diagnosing a disease in a person based on the spectral signature determined in the Raman spectrum.

27. The sensor-network system of claim 26, wherein the body fluid includes blood, saliva, urine, serum, tear, sweat, stomach fluid, hydrothorax, ascites, CSF, sperm, or a secrete body fluid.

28. The sensor-network system of claim 26, wherein the disease is selected from the group consisting of lung cancer, breast cancer, stomach cancer, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, pancreas cancer, head cancer, neck cancer, skin cancer, liver cancer, liver cirrhosis, a failing kidney, HIV (virus), diabetes, Alzheimer's disease, Parkinson disease, smoking status, and drug addiction.

29. The sensor-network system of claim 26, wherein the disease includes an illicit use of a drug selected from a group consisting of heroin, methamphetamine, cocaine, caffeine, morphine, codeine, amphetamine, ephedrine, papaverine, narcotine, acetyl codeine, methamphetamine HCl, ketamine HCl, codeine $H_3PO_4$, meperidine HCl (pethidine), triazolam, secobarbital, hypaconitine, and MDMA.

30. The sensor-network system of claim 14, wherein the sample material is extracted from a food product.

31. The method of claim 14, wherein the chemical or biological substance is selected from the group consisting of melamine, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, enorfloxacin, rhodanmine B, benzoic acid, hyposulfurous acid, sodium formaldehyde, formaldehyde, phthalates, dioxins, Pd, Cd Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants, food preservants, sweeteners, emulsifier, swelling agents overdose, bleach, sulfer suffumigation, color protectants, $TiO_2$, benzoyl peroxide, and $KAlSO_4$.

32. The sensor-network system of claim 14, wherein the sample material comprises a body fluid obtained from a person or an animal, the method further comprising: diagnosing a disease in the person based on the spectral signature determined in the Raman spectrum.

33. The sensor-network system of claim 32, wherein the body fluid includes blood, saliva, urine, serum, tear, sweat, stomach fluid, hydrothorax, ascites, CSF, sperm, or a secrete body fluid.

34. The sensor-network system of claim 32, wherein the disease is selected from the group consisting of lung cancer, breast cancer, stomach cancer, ulcer cancer, ovarian cancer, uterus cancer, cervix cancer, oral cancer, esophageal cancer, thyroid cancer, larynx cancer, leukemia, colon cancer, bladder cancer, prostate cancer, bronchus cancer, pancreas cancer, head cancer, neck cancer, skin cancer, liver cancer, liver cirrhosis, a failing kidney, HIV (virus), diabetes, Alzheimer's disease, Parkinson disease, smoking status, and drug addiction.

35. The sensor-network system of claim 32, wherein the disease includes an illicit use of a drug selected from a group consisting of heroin, methamphetamine, cocaine, caffeine, morphine, codeine, amphetamine, ephedrine, papaverine, narcotine, acetyl codeine, methamphetamine HCl, ketamine HCl, codeine $H_3PO_4$, meperidine HCl (pethidine), triazolam, secobarbital, hypaconitine, and MDMA.

* * * * *